(12) United States Patent
Hoffman et al.

(10) Patent No.: US 12,059,341 B2
(45) Date of Patent: Aug. 13, 2024

(54) SYSTEMS, DEVICES AND METHODS OF MAKING PROSTHETIC IMPLANTS HAVING SELF-SEALING MEMBRANES FOR CLOSING PUNCTURES AND PREVENTING LEAKS

(71) Applicant: Mentor Worldwide LLC, Irvine, CA (US)

(72) Inventors: Michael Hoffman, Hillsborough, NJ (US); Sriram Natarajan, Hillsborough, NJ (US); Annmarie Mullen, Bridgewater, NJ (US); Hector Javier Toro Estrella, Lake Forest, CA (US)

(73) Assignee: MENTOR WORLDWIDE LLC, Irvine, CA (US)

( * ) Notice: Subject to any disclaimer, the term of this patent is extended or adjusted under 35 U.S.C. 154(b) by 160 days.

(21) Appl. No.: 17/675,122

(22) Filed: Feb. 18, 2022

(65) Prior Publication Data

US 2022/0280281 A1  Sep. 8, 2022

Related U.S. Application Data

(60) Provisional application No. 63/157,285, filed on Mar. 5, 2021.

(51) Int. Cl.
*A61F 2/12* (2006.01)
*B29C 55/00* (2006.01)
(Continued)

(52) U.S. Cl.
CPC ............. *A61F 2/12* (2013.01); *B29C 55/005* (2013.01); *B29C 55/12* (2013.01);
(Continued)

(58) Field of Classification Search
CPC .. A61F 2/12; A61F 2240/001; B29K 2083/00
See application file for complete search history.

(56) References Cited

U.S. PATENT DOCUMENTS 4,455,691 A * 6/1984 Van Aken Redinger ................... A61F 2/12 528/901
4,472,226 A    9/1984 Redinger et al.
(Continued)

FOREIGN PATENT DOCUMENTS

| CA | 2931028 | 5/2014 |
|---|---|---|
| EP | 2919709 | 7/2019 |

(Continued)

OTHER PUBLICATIONS

International Search Report issued in corresponding International Application No. PCT/IB2022/051692, dated May 30, 2022, 5 pages.

*Primary Examiner* — Suzette J Gherbi
(74) *Attorney, Agent, or Firm* — TROUTMAN PEPPER HAMILTON SANDERS LLP

(57) ABSTRACT

A method of making a self-sealing membrane for a prosthetic implant includes applying tension to a first layer of a cured elastomeric material to stretch the first layer, and while the first layer remains stretched, applying a second layer of an uncured elastomeric material over a first major surface of the first layer. After the second layer is cured, the tension on the first layer is released, whereupon the first layer returns to a non-stretched configuration for holding the second layer in contraction. The method includes, while the first layer remains stretched, applying a third layer of an uncured elastomeric material over a second major surface of the first layer. After curing the second and third layers, tension is released from the first layer, which returns to the non-stretched configuration for holding the second and third layers in contraction.

24 Claims, 32 Drawing Sheets

(51) Int. Cl.
  *B29C 55/12* (2006.01)
  *B29K 83/00* (2006.01)
  *B29L 31/00* (2006.01)

(52) U.S. Cl.
  CPC ..... *A61F 2240/001* (2013.01); *B29K 2083/00* (2013.01); *B29L 2031/7532* (2013.01)

(56) References Cited

U.S. PATENT DOCUMENTS

| | | | |
|---|---|---|---|
| 4,960,425 A | 10/1990 | Yan et al. | |
| 5,022,942 A | 6/1991 | Yan et al. | |
| 5,049,393 A * | 9/1991 | Noon | A61L 33/025 523/112 |
| 5,314,653 A | 5/1994 | Haralambopoulos | |
| 6,428,571 B1 * | 8/2002 | Lentz | A61L 27/16 623/1.4 |
| 6,743,254 B2 * | 6/2004 | Guest | A61F 2/12 623/8 |
| 8,070,828 B2 * | 12/2011 | Shannon | A61F 2/7812 623/36 |
| 8,690,943 B2 * | 4/2014 | Schuessler | A61B 90/02 623/8 |
| 8,870,952 B2 * | 10/2014 | Holland | F16K 15/202 623/8 |
| 8,981,621 B2 * | 3/2015 | Pelrine | F04B 35/045 310/800 |
| 9,351,824 B2 | 5/2016 | Renke | |
| 9,463,087 B2 * | 10/2016 | Hristov | A61F 2/12 |
| 9,700,404 B2 | 7/2017 | Martin et al. | |
| 10,010,395 B2 * | 7/2018 | Puckett | D04H 1/728 |
| 10,070,951 B2 | 9/2018 | Renke | |
| 10,391,199 B2 * | 8/2019 | Liu | A61L 27/18 |
| 10,765,506 B2 * | 9/2020 | Chitre | A61B 90/02 |
| 10,820,984 B2 | 11/2020 | Renke | |
| 11,202,853 B2 * | 12/2021 | Liu | A61L 27/26 |
| 2003/0149481 A1 * | 8/2003 | Guest | A61F 2/12 623/8 |
| 2005/0131325 A1 * | 6/2005 | Chen | A61M 39/0208 602/41 |
| 2009/0030515 A1 * | 1/2009 | Schuessler | A61F 2/12 623/8 |
| 2010/0049316 A1 * | 2/2010 | Schuessler | A61F 5/003 623/8 |
| 2011/0270391 A1 * | 11/2011 | Chitre | A61F 2/12 623/8 |
| 2011/0276133 A1 * | 11/2011 | Liu | A61L 31/06 521/61 |
| 2011/0288639 A1 * | 11/2011 | Trilokekar | A61F 2/12 623/8 |
| 2013/0023987 A1 * | 1/2013 | Liu | A61L 27/50 427/2.24 |
| 2013/0131799 A1 * | 5/2013 | Schuessler | B29C 73/18 427/2.24 |
| 2014/0088703 A1 | 3/2014 | Schuessler | |
| 2014/0094662 A1 * | 4/2014 | Van Epps | A61B 5/0053 600/301 |
| 2016/0022866 A1 * | 1/2016 | Liu | A61F 2/12 427/2.24 |
| 2016/0081783 A1 * | 3/2016 | Puckett | D01F 6/12 264/465 |
| 2019/0000608 A1 * | 1/2019 | Renke | B29C 41/08 |
| 2020/0038550 A1 * | 2/2020 | Liu | A61L 27/18 |
| 2023/0285974 A1 * | 9/2023 | Siu | G16B 50/30 422/400 |

FOREIGN PATENT DOCUMENTS

| | | | |
|---|---|---|---|
| WO | 2014078498 | 5/2014 | |
| WO | 2017184962 | 10/2017 | |
| WO | 2020055740 | 3/2020 | |
| WO | WO-2023021345 A1 * | 2/2023 | A61B 90/02 |

* cited by examiner

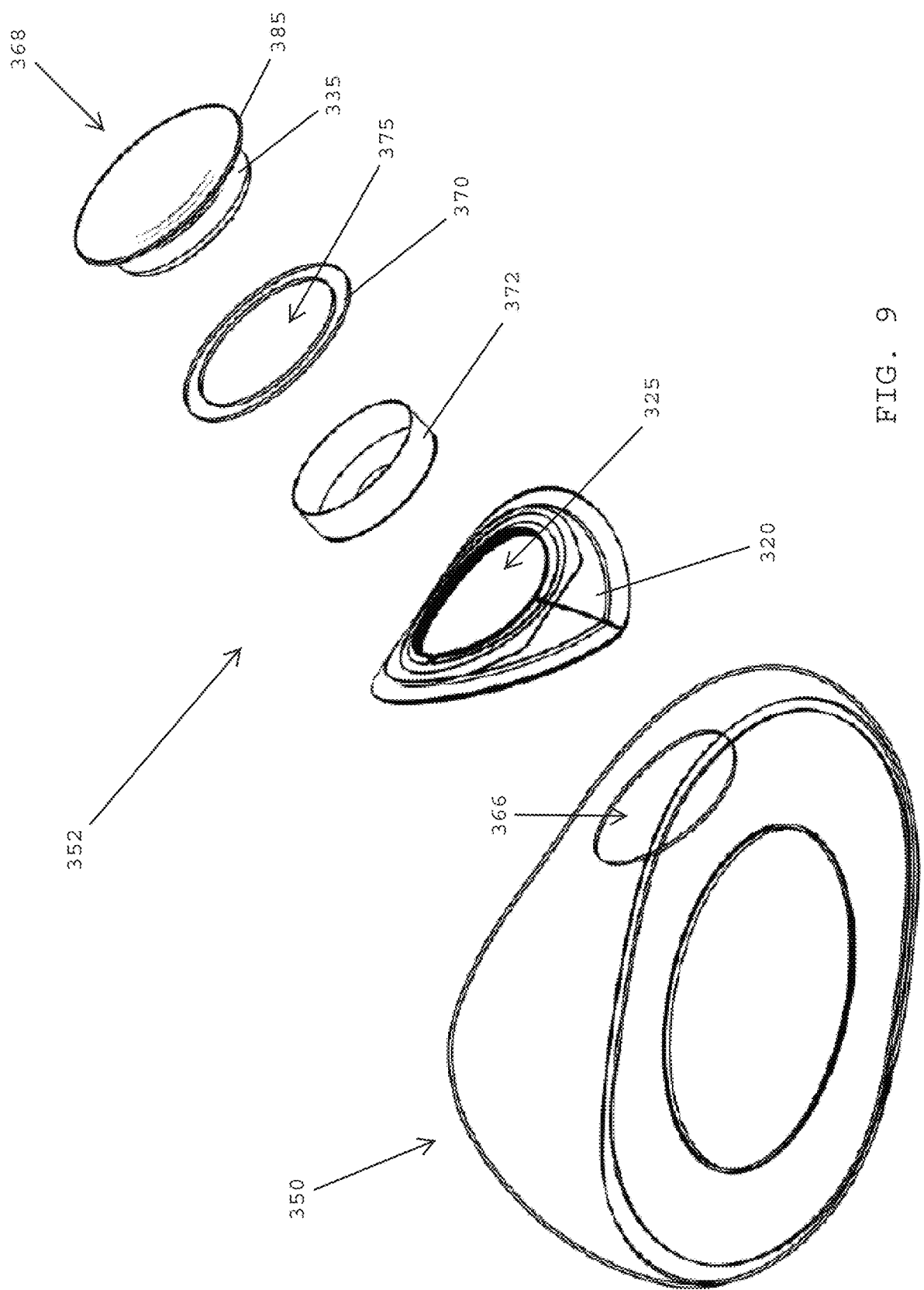

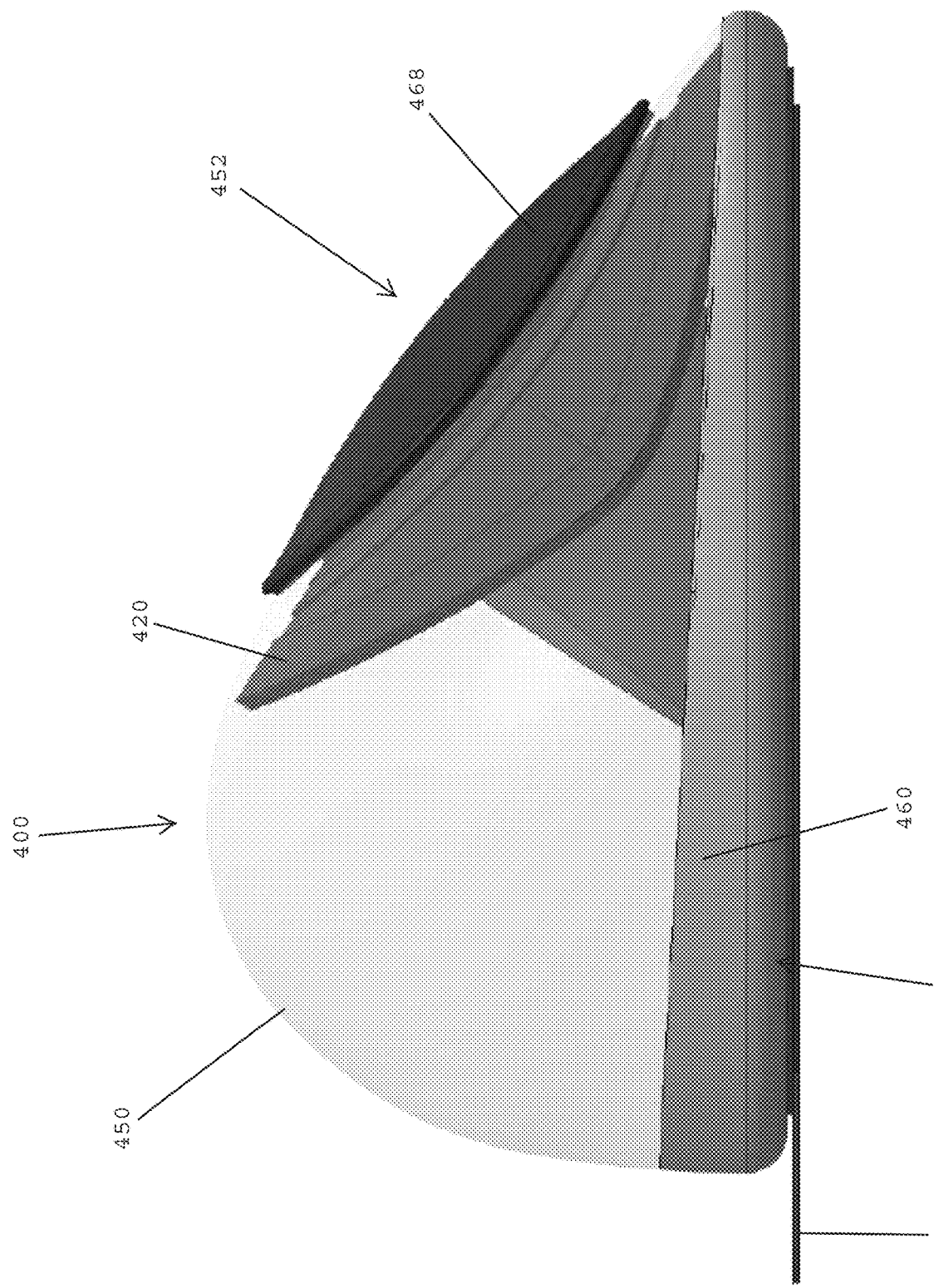

SYSTEMS, DEVICES AND METHODS OF MAKING PROSTHETIC IMPLANTS HAVING SELF-SEALING MEMBRANES FOR CLOSING PUNCTURES AND PREVENTING LEAKS

CROSS-REFERENCE TO RELATED APPLICATIONS

The present patent application claims benefit of U.S. Provisional Application Ser. No. 63/157,285, filed on Mar. 5, 2021, the disclosure of which is hereby incorporated by reference herein.

BACKGROUND OF THE INVENTION

Field of the Invention

The present patent application is generally related to prosthetic implants and is more specifically related to systems, devices and methods of making self-sealing membranes for prosthetic implants, such as tissue expanders, that have one or more zones under contraction for closing punctures and preventing fluid leaks.

Description of the Related Art

Prosthetic implants, such as tissue expanders, are typically used to replace or augment body tissue. In the case of the female breast, it may become necessary to remove some or all of the mammary gland and surrounding tissue in order to treat breast cancer. This surgery typically leaves a void that can be filled with an implantable breast prosthesis that supports surrounding tissue and provides a normal body appearance, thereby eliminating much of the shock and depression that often follows breast cancer surgeries. Implantable breast prostheses are also used for breast augmentation procedures.

Tissue expanders are a type of implantable devices that are placed beneath the skin and then gradually inflated to stretch the overlying tissue. Tissue expanders are commonly used to either create a pocket for receiving a permanent prosthesis or to generate an increased skin surface area in anticipation of the new skin being utilized for grafting or reconstruction. After implantation, a solution, such as saline, is periodically injected into the tissue expander to increase the volume of the expander. Between injections, the surrounding skin is permitted to stretch and grow to create the increased skin surface. The solution (e.g., saline solution) may also be withdrawn from the tissue expander to reduce its volume.

Implantable prostheses and tissue expanders are usually formed of a shell of an elastomeric material (e.g., a silicone shell). Such devices are typically manufactured by dipping an appropriately sized and shaped mandrel into a biocompatible elastomer, such as silicone. Once the shell has been formed, it is removed from the mandrel. The dip-molding process results in the formation of a shell that has a mandrel opening, e.g., a circular hole, in one of its faces. The mandrel opening is subsequently covered with a patch that seals the hole to form a fluid impervious implant shell. The patch may be attached to the implant shell using silicone elastomers or other similar biocompatible elastomers.

Tissue expanders typically have integrated injection ports that are used for expanding shells. Over as period of time, a fluid, such as saline, is introduced through the injection ports to fill and expand the shells in order to enlarge the breast pocket. A potential failure mode for a mammary implant is accidental puncture of the shell outside the injection port, thereby resulting in fluid leaks and deflation of the shell, which may require another operation to remove and/or replace the tissue expander.

There have been many efforts directed to making mammary implants. For example, U.S. Pat. No. 4,960,425 to Yan et al., assigned to Mentor Worldwide LLC, the disclosure of which is hereby incorporated by reference herein, teaches a surgical prosthesis having a textured exterior surface formed of non-absorbent material, which is substantially free of pores and interstices. The device is usable for mammary and other implants. As shown in FIG. 2 of the '425 patent, an unpatched surgical prosthesis, such as for use as a mammary implant, is stretched over a flat or low curvature disk having a circular, oval or other suitable shaped cross-section. The majority of the exterior surface of the prosthesis is located on the upper side of the disk. A layer or multiple layers of unvulcanized or partially vulcanized silicone with a total thickness of 0.003 inches to 0.10 inches covers the upper surface of the prosthesis. The silicone covering is disposed across almost the entire exterior surface of the prosthesis such that no seam will appear visible at the top or substantially any of the sides of the finished prosthesis. The silicone covering is covered with a porous or textured medium, such as foam, a perforated screen or a specially molded form having a textured surface of the particular desired design and topography. The entire assembly including the disk, prosthesis, silicone layer and porous or textured medium is then compressed using either cold or hot compressive platens. After compression, the platens are removed and the medium is also removed leaving a texturized imprint in the silicone layer. The prosthesis with the imprinted texturized silicone layer is then removed from the disk and the prosthesis with the imprinted silicone layer is cured at vulcanizing temperatures.

There have been many efforts directed to providing implantable prostheses that are designed to prevent fluid leaks. For example, U.S. Pat. No. 6,743,254 to Guest et al., assigned to Mentor Worldwide LLC, the disclosure of which is hereby incorporated by reference herein, teaches a mammary prosthesis having a self-sealing area in the upper pole region of the anterior face. The self-sealing area is greater than that of a traditional filling port, and reduces the severity of the consequences of an inadvertent puncture by a hypodermic needle during the filling process. In addition, the self-sealing area is thicker than the material in the other areas of the prosthesis, causing fluid introduced to the prosthesis to stay in the lower pole region of the prosthesis, making the shape of the prosthesis appear more like that of a natural breast.

U.S. Pat. No. 8,870,952 to Holland et al., assigned to Ethicon, Inc. of Somerville, New Jersey, the disclosure of which is hereby incorporated by reference herein, teaches an expandable implant including an implant shell having an opening and a valve assembly for closing the opening. The valve assembly has a first elastic patch, and a second elastic patch juxtaposed with the first elastic patch. A major face of the first elastic patch opposes a major face of the second elastic patch. The opposing major faces have a bonded area in which the opposing faces are joined together and an unbonded area in which the opposing major faces are not joined together and are free to move away from one another. A plug is disposed between the opposing major faces. A first opening extends through the first elastic patch and a second opening extends through the second elastic patch. The first and second openings are offset from one another and the unbonded area defines an elongated channel extending between the first and second openings.

U.S. Pat. No. 9,700,404 to Martin et al., assigned to Ethicon, Inc. of Somerville, New Jersey, the disclosure of which is hereby incorporated by reference herein, teaches a tissue expander having an outer shell configured to retain a fluid, and an injection dome having a self-sealing septum region arranged through the outer shell. The injection dome is adapted to accept a hypodermic needle in order to fill the outer shell with fluid. The injection dome has a self-sealing patch arranged around the injection dome and along the outer shell, which includes a first sheet having a first sheet perimeter and forming a first central opening, a second sheet having a second sheet perimeter and forming a second central opening, an outer washer arranged between the first and second sheets at the first sheet perimeter and the second sheet perimeter, and a second washer arranged between the first and second sheets at the first central opening and the second central opening. The first sheet and the second sheet bound an annular space formed between the outer washer and the inner washer. The annular space is filled with a self-sealing material, such as a hydrophobic material, having a viscosity which is sufficiently high to prevent the self-sealing material from flowing outside the annular space when either the first or second sheet is punctured with a hypodermic needle, but low enough in viscosity so that the self-sealing material flows to close a track made by a hypodermic needle that has punctured the first or second sheet. The self-sealing material may be liquid silicone rubber, cohesive gel, sensitive gel, or memory gel.

U.S. Pat. Nos. 9,351,824 and 10,070,951 to Renke, both assigned to ImplantAdjust, LLC or Point Roberts, Washington, disclose an adjustable implant for volumetrically altering, replacing, expanding, or augmenting tissues. The implant includes an elastomeric membrane enclosed or partially enclosed about a main chamber. The implant is adapted to expand when filled with a fluid. The membrane includes an outer zone formed from at least one outer elastomeric layer; an inner zone formed from at least one inner elastomeric layer; and a middle zone formed from at least one elastomeric middle layer that is positioned between a least a portion of the outer zone and at least a portion of the inner zone. The implant is configured so that the middle zone is under contraction from a contracting force provided by the outer zone or the inner zone.

In spite of the above advances, there remains a need for improved mammary implants, prosthetic implants, and tissue expanders having effective and reliable self-sealing capabilities incorporated therein. There also remains a need for mammary implants, prosthetic implants, and tissue expanders having self-sealing membranes, self-sealing sheets, and self-sealing shell constructions that do not leak when punctured with a needle, and that do not leak when expanded to target volumes and pressures.

SUMMARY OF THE INVENTION

A method of making a self-sealing membrane for a prosthetic device desirably includes applying tension to a first layer of a cured elastomeric material to stretch the first layer, and while the first layer remains stretched, applying a second layer of an uncured elastomeric material over a first major surface of the first layer and curing the second layer of the elastomeric material.

In one embodiment, after the second layer is cured, tension is released from the first layer whereupon the first layer returns to a non-stretched configuration for holding the second layer in contraction.

In one embodiment, the first layer is a shell for a prosthetic implant, and the applying tension step includes stretching the shell over a disk for exposing the first major surface.

In one embodiment, the disk has a flat major surface, and stretching the shell over the disk conforms the first major surface of the shell to the shape of the flat major surface of the disk.

In one embodiment, curing the second layer preferably includes applying heat to the second layer.

In one embodiment, the second layer may be compressed into the first major surface of the first layer, such as by using a press.

In one embodiment, the compressing step may occur during the applying heat step. In one embodiment, the compressing step may occur before the applying heat step.

In one embodiment, a method may include, while the first layer remains stretched, applying a third layer of an uncured elastomeric material over a second major surface of the first layer and curing the third layer of the elastomeric material.

In one embodiment, after the second and third layers are cured and the tension is released from the first layer, the first layer returns to the non-stretched configuration for holding the second and third layers in contraction.

In one embodiment, the first layer includes a cured silicone elastomer, and the second and third layers may include an uncured silicone elastomer.

In one embodiment, a fixture may be used for applying tension for stretching the first layer within a plane.

In one embodiment, curing the second and third layers may include applying heat to the second and third layers.

In one embodiment, the second and third layers may be compressed into the respective first and second major surfaces of the first layer.

In one embodiment, the compressing step may occur during the applying heat step. In one embodiment, the compressing step may occur before the applying heat step.

In one embodiment, a self-sealing membrane for a prosthetic implant has a three-layer construction including a middle layer of an elastomeric material having first and second major surfaces, a first outer layer of an elastomeric material overlying the first major surface of the middle layer, and a second outer layer of an elastomeric material overlying the second major surface of the middle layer, whereby the middle layer of the elastomeric material holds the first and second outer layers of the elastomeric material in contraction.

In one embodiment, the self-sealing membrane is preferably secured to an inner surface of a silicone shell of a prosthetic implant.

In one embodiment, the self-sealing membrane preferably extends around an outer perimeter of an injection port of a prosthetic implant.

In one embodiment, the self-sealing membrane may be secured to a posterior region of a silicone shell of a prosthetic implant.

In one embodiment, the self-sealing membrane preferably defines a self-sealing base that covers an inner surface of the silicone shell at the posterior region of the silicone shell.

In one embodiment, a self-sealing sheet includes two or more of the self-sealing membranes having the three-layer construction disclosed herein.

In one embodiment, major surfaces of adjacent ones of the self-sealing membranes having the three-layer construction are laminated together.

In one embodiment, a self-sealing sheet may include a first self-sealing membrane having the three-layer construction, a second self-sealing membrane having the three-layer construction being laminated to an exposed major surface of the first self-sealing membrane, and a third self-sealing membrane having the three-layer construction being laminated to an exposed major surface of the second self-sealing membrane.

The self-sealing sheet having two of more of the self-sealing membranes having the three-layer construction may be incorporated into an injection port assembly of a prosthetic implant. In one embodiment, the self-sealing sheet may be disposed between an injection dome and a needle guard of an injection port assembly.

In one embodiment, a shell (e.g., a silicone shell) for a prosthetic implant (e.g., a tissue expander) preferably has self-sealing properties incorporated therein, which prevent the shell from leaking fluid when punctured by a needle or a sharp object.

In one embodiment, the shell has a two-layer construction with a first layer and a second layer, whereby the second layer is held in contraction by the first layer.

In one embodiment, the first layer may be formed by depositing and curing a biocompatible elastomeric shell layer (e.g., a silicone shell) on a three-dimensional (3D) tool, such as a mandrel. In a relaxed state (i.e., with no external forces exerted on the shell), the shell has an inherent interior three-dimensional (3D) volume and a two-dimensional (2D) surface area.

In one embodiment, the first layer may be a shell that is stretched in a plane so that the surface area of the shell is greater than the inherent surface area of the shell in the relaxed state, however, the encompassed volume of the stretched shell is less than the inherent 3D volume of the shell in the relaxed state. After the shell is stretched, the second layer of an uncured biocompatible elastomeric material (e.g., uncured silicone material) may be deposited onto the stretched shell and cured, while the shell is held in the stretched state. After curing of the second layer and release of the two-layer construction back to a relaxed state, the second layer is held in contraction by the first layer, resulting in the second layer being configured to contract and close any holes that may be formed in the two-layer construction (e.g., when a needle punctures the self-sealing structure).

Different systems, devices and methods may be used for stretching the first layer of a self-sealing membrane to increase the surface area of the first layer. In one embodiment, the first layer (i.e., a silicone shell) is stretched over a flat disk, whereby the outer periphery of the shell wraps over the outer periphery of the disk to keep the shell in place on the disk. In a second embodiment, the first layer may be stretched by using biaxial and/or a multi-axial tensioning process for griping and stretching the first layer.

In one embodiment, the first layer is preferably stretched in different directions within a single plane.

In one embodiment, a prosthetic implant (e.g., tissue expander) may have one or more self-sealing membranes (e.g., elastomeric membranes) that are designed to prevent fluid leaks if an implant shell and/or the one or more self-sealing membranes are punctured by a needle.

In one embodiment, the self-sealing elastomeric membranes may be made of silicone materials, however, other elastomeric materials may be used for making the self-sealing membranes disclosed herein.

When designing, manufacturing and testing mammary implants, tissue expanders, and breast prostheses, the terminology "self-sealing" is defined as the ability of a material to seal after being punctured (e.g., by a filling needle) so as to prevent the filler material (e.g., saline; gel) within the implant from escaping, even when the implant is put under load. Self-sealing requirements for breast tissue expanders are defined in ASTM F1441-03.

In one embodiment, a method of making an implant (e.g., a breast tissue expander) having self-sealing capabilities preferably includes stretching a shell (e.g., a silicone shell) onto a substrate having a major, flat surface (i.e., a disk) to expose a flat, uniform surface on the shell.

In one embodiment, after being placed over the disk, the shell is stretched by the disk and has the exposed, flat, uniform surface that generally conforms to the shape of the underlying major, flat surface of the disk.

In one embodiment, with the shell stretched by the disc, a layer of an uncured biocompatible elastomeric material (e.g., unvulcanized polysiloxane elastomer) may be deposited onto the exposed, flat surface of the stretched shell. The layer of the uncured elastomeric material is desirably trimmed to the edge of the disk.

In one embodiment, the uncured elastomer layer (e.g., an uncured silicone layer) is cured on the shell, while the shell is being stretched by the stretching disk.

In one embodiment, the layer of the uncured elastomeric material may be cured during a pressing step, whereby platens are used to press the first and second layers together. In one embodiment, the platens may be heated. The heat preferably cures the second layer that has been added to the shell.

In one embodiment, the second layer that has been added to the shell may be cured by placing an assembly of the disk, the shell, and the uncured elastomer layer into an oven having temperatures that are adapted to cure the second layer.

In one embodiment, once the second layer is fully cured on the shell (i.e., the first layer), the shell and the cured second layer may be removed from the stretching disk. Upon removing the shell from the disk, the shell contracts back into its original shape.

The resulting seal-sealing membrane has a two-layer construction, whereby a second zone (i.e., the cured elastomeric layer) of the self-sealing membrane is held in contraction by a first zone (i.e., the shell). In one embodiment, the initial shell layer that was stretched over the disk holds the added elastomeric layer (i.e., the second zone) in contraction.

In one embodiment, the above-describe method requires the initial silicone shell layer to be elongated in a two-dimensional planar manner.

In one embodiment, a foam layer may be placed into the press prior to closing the platens of the press. In one embodiment, a foam layer is placed between the uncured elastomeric layer and the platen prior to closing the press for compressing the assembly of the first layer (e.g., the silicone shell) and the second layer (e.g., the uncured elastomeric layer).

In one embodiment, the volume of the shell is not significant in the process, and the process of making a self-sealing membrane does not require the volume to be greater during the stretched state (and upon application of the additional silicone sheeting) compared to its initial state. For example, in one embodiment, the surface area of the stretched shell may be 110% to 250% compared to its relaxed state, whereby the encompassed volume of the stretched shell may be 30% to 90% compared to its relaxed state.

In one embodiment, a self-sealing membrane may have a plurality of layers that are under contraction, which can be achieved by running the above-disclosed process multiple times.

For example, one layer can be added as described above, and a second layer can be added by inverting the shell, stretching the shell back onto the disk, and repeating the above-described process to add a second uncured elastomeric layer.

In one embodiment, a self-sealing membrane may include a three-layer construction including two outer layers under contraction and an intermediate layer that holds the two outer layers in contraction. In one embodiment, the self-sealing membrane having the three-layer construction may be achieved by using a modified stretching disk fixture that allows for the application of a first uncured elastomeric layer on a first major surface of a shell and the application of a second uncured elastomeric layer on a second major surface of the shell. In one embodiment, the shell is stretched as the first and second uncured elastomeric layers are applied to the shell, and the shell remains stretched as the first and second elastomeric layers are cured.

In one embodiment, when performing a process of applying layers of uncured elastomeric material multiple times, the stretching disks may be different sizes resulting in layers that have different levels of contraction. For example, an outermost layer of a self-sealing membrane may have the lowest amount of contraction and an innermost layer of the self-sealing membrane may have the highest amount of contraction, which may provide a "bottle-neck" mechanism for self-sealing. Furthermore, differential contraction between layers may result in a desired curvature of the curved membrane, despite the process being performed in a planar manner In one embodiment, a method of making an implant having self-sealing properties may include simultaneously stretching multiple shells onto a stretching disk, and using uncured elastomeric layers between the shells for bonding the adjacent shells together. As a result, contraction of the uncured elastomeric material layers, or differential contraction of the shells if they have different sizes, can result in the formation of a self-sealing implant or expander.

In one embodiment, the uncured elastomeric material that is deposited onto a stretched shell does not have to be applied to the shell in sheet form. In one embodiment, the uncured elastomeric material may be deposited using other processes such as spraying or dipping the uncured elastomeric material onto an exposed surface of a stretched shell.

In one embodiment, the consistency/durometer and thickness/amount of the one or more uncured elastomeric layers that are applied to a stretched shell may differ, including but not limited to high consistency silicone, liquid silicone, or gels. In one embodiment, the stretched shell may have higher tensile stiffness than the uncured elastomeric layers in order to increase the amount of compression imparted in those layers.

In one embodiment, a biaxial tensioning process may be used for making a self-sealing membrane having first and second outer layers that are under contraction and an intermediate layer located between the first and second outer layers and that holds the first and second outer layers under contraction.

In one embodiment, a method of making a self-sealing membrane preferably includes using a fixture for securing an outer periphery of an intermediate layer (e.g., a vulcanized silicone elastomer sheet) and expanding the size of the fixture for stretching the intermediate layer in orthogonal directions. In one embodiment, the intermediate layer is preferably stretched within a single plane so that the intermediate layer has first and second major surfaces that are flat.

In one embodiment, a first layer of an uncured elastomer (e.g., unvulcanized polysiloxane elastomer) may be applied to the first major surface of the intermediate layer, and a second layer of an uncured elastomer (e.g., unvulcanized polysiloxane elastomer) may be applied to the second major surface of the intermediate layer.

In one embodiment, the first and second uncured outer layers and the intermediate layer are desirably pressed together and the three-layer structure may be cured by using heat. In one embodiment, a press having platens may be used for pressing the three layers together. In one embodiment, the platens may be heated. In one embodiment, a roller may be used for applying pressure to the layers.

In one embodiment, once the three-layer construction is fully cured, the outer periphery of the intermediate layer may be released from the fixture, whereupon the intermediate layer returns to its original, non-stretched configuration.

In one embodiment, when the intermediate layer returns to its original, non-stretched configuration, the intermediate layer holds the first and second outer layers in contraction.

In one embodiment, a self-sealing sheet may include a plurality of self-sealing membranes, each self-sealing membrane having a three-layer construction. In one embodiment, adjacent self-sealing membranes, each having three layers, may be joined or laminated together, such as by using unvulcanized material (e.g., unvulcanized elastomeric sheets) between adjacent three-layer, self-sealing membranes.

In one embodiment, a plurality of differentially contracted silicone layers may be achieved by running the above-described process multiple times, or having a fixture that elongates multiple parallel vulcanized silicone elastomer sheets, with the ability to adhere unvulcanized material in between.

In one embodiment, a cured layer of elastomeric material (e.g., a silicone shell) may be stretched over a stretching disk having a curved surface. The stretched cured layer of elastomeric material preferably has an exposed surface that is curved to conform to the shape of the curved surface of the stretching disk. In one embodiment, an uncured elastomeric material is applied over the curved surface of the stretched, cured layer, whereupon the uncured material conforms to the curved shape of the stretched, cured layer. After curing, when the first layer is removed from the disk, the self-sealing membrane defines sheeting that is concave towards the side that was cured under greater elongation.

In one embodiment, the stretching process does not have to be square or rectangular in nature. In one embodiment, a stretching fixture may be circular for radially stretching the cured elastomeric layer (e.g., a silicone shell).

In one embodiment, a seal-sealing membrane has a three-layer construction in which the outer zones (e.g., first and second outer layers) are held in contraction by a middle zone (e.g., an intermediate layer).

In one embodiment, the self-sealing membrane may be used to cover a portion of shell of a prosthetic implant. In one embodiment, the self-sealing membrane may replace a reinforcement patch that is sold under the registered trademark BUFFERZONE® by Mentor Worldwide LLC of Irvine, California, and that is used as a port protector for injection ports of implantable medical devices such as tissue expanders and breast implants.

In one embodiment, the self-sealing membrane disclosed herein is more pliable and easier to fold that conventional bladder-style sealing mechanisms. In one embodiment, the self-sealing membrane has improve tensile properties due to the incorporation of the compressed layers, such as increased elongation to failure, increased ultimate breaking force, and increased tensile stiffness.

In one embodiment, the self-sealing membrane disclosed herein has a homogenous construction with self-sealing capabilities throughout the entire surface area of the self-sealing membrane.

In one embodiment, the self-sealing membrane disclosed herein is easier and faster to make because its construction does not require the use of silicone gel or viscous fluids.

In one embodiment, a self-sealing membrane may be used to cover an anterior region of a shell of a prosthetic implant, such as a tissue expander.

In one embodiment, a self-sealing membrane preferably surrounds the injection port or an injection zone of a tissue expander shell.

In one embodiment, a self-sealing membrane disclosed herein may be used for covering other regions of a shell of a prosthetic implant. For example, a tissue expander (e.g., a breast tissue expander) may have suture tabs located in a posterior region of a shell for securing the tissue expander to surrounding tissue. Thus, in one embodiment, a self-sealing membrane may cover a base, a base patch, a base patch having suture tabs, a posterior end and/or a posterior radius of a tissue expander to protect those areas of the shell that are at risk of accidental needle puncturing, specifically during fixation of the tissue expander to the surrounding tissue.

In one embodiment, the self-sealing membranes and self-sealing structures disclosed herein may be applied throughout a shell to ensure coverage and leak prevention in other desired regions.

In one embodiment, the self-sealing membranes and self-sealing structures disclosed herein may be continuously adjoined or form an overlapping patchwork of self-sealing sheeting that may be applied to cover an entire shell.

Standard injection ports used in breast tissue expanders typically use molded silicone as the self-sealing material, and typically rely on a combination of thickness and compression from the outer metal injection port assembly.

In one embodiment, a self-sealing membrane or self-sealing structure disclosed herein may be incorporated into an injection port of a tissue expander. The seal-sealing construction disclosed herein provides superior self-sealing properties when compared to an equivalent thickness of molded silicone, and therefore can also be used as the injection port material.

In one embodiment, the self-sealing capabilities of an injection port may be improved by using a plurality of the self-sealing membranes that are joined together, whereby the plurality of the joined self-sealing membranes are thinner than the typical, prior art molded silicone material for this use.

These and other preferred embodiments of the present patent application will be described in more detail herein.

BRIEF DESCRIPTION OF THE DRAWINGS

FIG. 9 is an exploded view of a shell having an injection port opening, and an injection port assembly that is assembled with the injection port opening, the injection port assembly including an injection dome, an injection dome sealing washer, a needle guard with magnet, and a self-sealing membrane, in accordance with one embodiment of the present patent application.

FIG. 12B is a side view of the breast tissue expander shown in FIG. 12A.

DETAILED DESCRIPTION OF PREFERRED EMBODIMENTS

Figure 1:
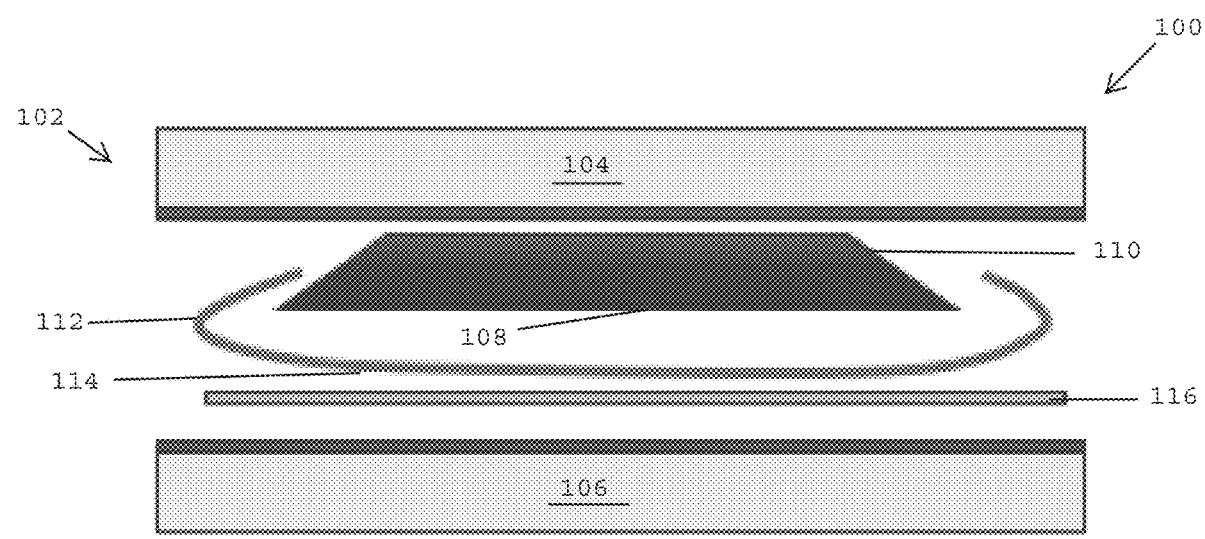
FIG. 1 is a schematic view of a system used for making a self-sealing membrane for an implant, in accordance with one embodiment of the present patent application.

Referring to FIG. 1, in one embodiment, a system 100 for making a self-sealing membrane for a shell (e.g., a mammary implant) preferably includes a press 102 having a top platen 104 and a bottom platen 106 that opposes one another. In one embodiment, the system 100 preferably includes a disk 108 (i.e., a stretching disk) having a flat major surface and an outer edge 110 that extends around an outer periphery of the disk. In one embodiment, a shell 112 (e.g., a cured silicone shell) is stretched over the disk 108 to expose a flat major surface 114 of the shell 112 that overlies the flat major surface of the disk 108.

In one embodiment, the shell 112 may be made using one or more of the systems, devices and methods disclosed in U.S. Pat. No. 4,472,226 to Redinger et al., U.S. Pat. No. 5,022,942 to Yan et al., or U.S. Patent Application Publication No. US 2014/0088703 to Schuessler, the disclosures of which are hereby incorporated by reference herein.

In one embodiment, the shell 112 may be made by dipping or spraying a mandrel with a biocompatible, curable material such as silicone, polymers, polyurethane, silicone-polyurethane co-polymers, elastomers or combinations thereof. After application of the biocompatible, curable material to the mandrel, the curable material is allowed to cure and the cured shell is removed from the mandrel.

In one embodiment, the disk 108 may be made of materials such as polymers, metal, wood, stone, and ceramic.

In one embodiment, a layer 116 of an uncured material (e.g., an uncured elastomer; an unvulcanized polysiloxane elastomer; an uncured silicone layer) is preferably placed onto the exposed flat surface 114 of the stretched shell 112 and trimmed to the outer edge 110 of the stretching disk 108. While the shell remains stretched over the stretching disk 108, the uncured layer 116 is desirably cured.

In one embodiment, the combination of the shell 112 and the uncured layer 116 may be placed into the press 102 of the system 100 so that pressing forces may be applied to the subassembly of the shell 112 and the uncured layer 116. The pressing forces are desirably applied by closing the press 102 by moving the top and bottom platens 104, 106 toward one another to compress the combination of the shell 112 and the uncured layer 116.

In one embodiment, during the pressing step, the top and bottom platens 104, 106 may be heated for applying heat to the combination of the shell 112 and the uncured layer 116. The heat preferably cures the uncured layer 116 for adhering the uncured layer to the expose flat surface 114 of the shell 112.

In one embodiment, the stretching disk 108, the stretched shell 112, and the uncured layer 116 may be placed into an oven at an elevated temperature for curing the uncured layer 116 while the stretched shell 112 remains on the stretching disk 108.

In one embodiment, heat may be applied directly to the assembly of the stretching disk 108, the shell 112, and the uncured layer 116 using heating elements such as one or more heat guns.

In one embodiment, once the uncured silicone layer 116 is fully cured for being adhered to the shell 112, the shell 112 and the cured layer 116 form a seal-sealing membrane that may be removed from the stretching disk 108. In one embodiment, due to the stretched state of the shell 112 on the stretching disk 108, upon removal from the stretching disk 108, the shell 112 portion of the self-sealing membrane contracts back into its original shape and the cured layer 116 is under contraction.

Figure 2:
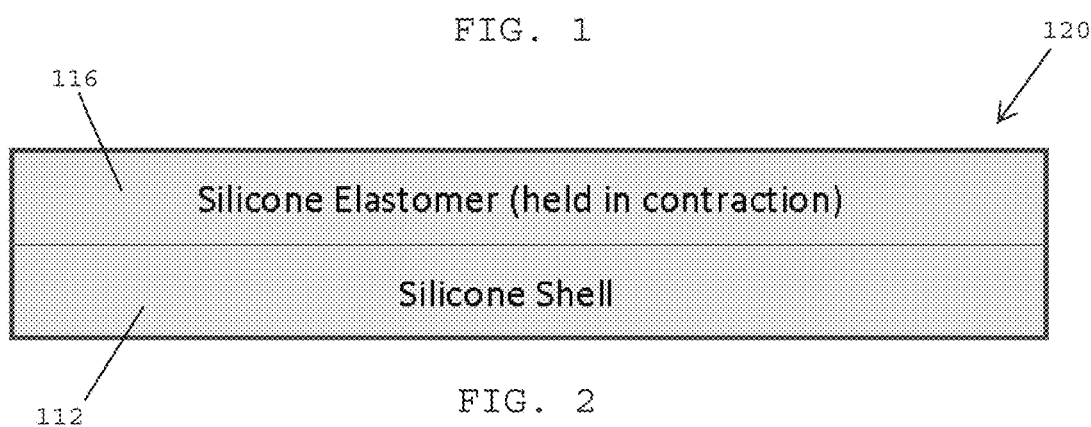
FIG. 2 is a schematic cross-sectional view of a self-sealing membrane having a two-layer construction with a first zone of the self-sealing membrane held in contraction by a second zone of the self-sealing membrane, in accordance with one embodiment of the present patent applications.

Referring to FIG. 2, in one embodiment, a self-sealing membrane 120 has a two-layer construction including a second layer 116 (i.e., a second zone) that is held in contraction by a first layer 112 (i.e., a first zone). Thus, after being removed from the disk 108 (FIG. 1), the shell layer 112 holds the added layer 116 in contraction.

Figure 3:
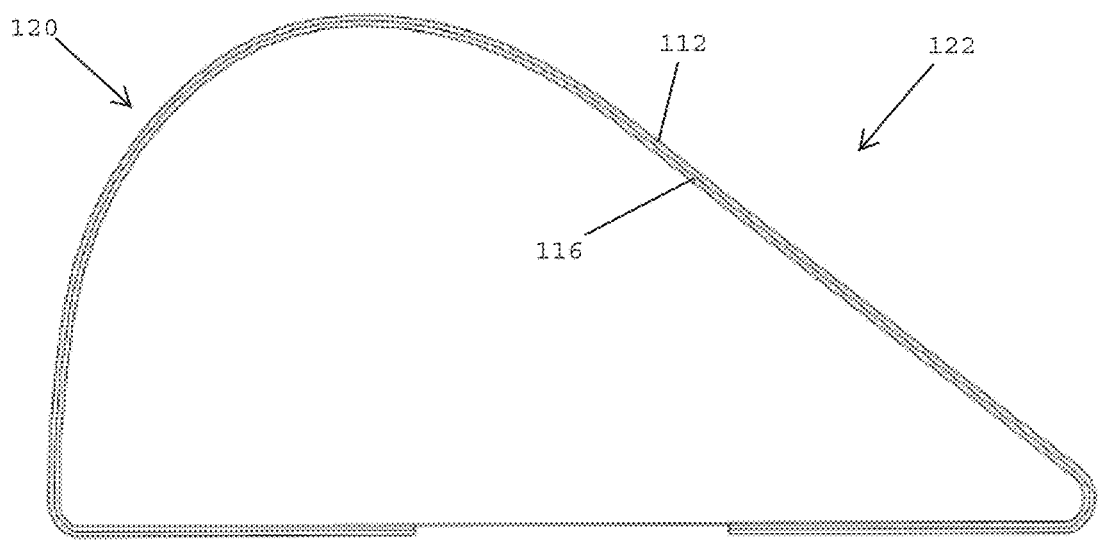
FIG. 3 is a cross-sectional view of a mammary implant shell including a self-sealing membrane having a two-layer construction with a first zone that is held in contraction by a second zone of the self-sealing membrane, in accordance with one embodiment of the present patent application.

Referring to FIG. 3, in one embodiment, a mammary implant 122 may include the self-sealing membrane 120 shown and described above in FIG. 2. The self-sealing membrane 120 may be made utilizing the system 100 shown and described above in FIG. 1. In one embodiment, the self-sealing membrane 120 may cover the entire area of the mammary implant 122 or a portion of the mammary implant 122 (e.g., an area surrounding an injection port). In one embodiment, the self-sealing membrane 120 includes the initial silicone shell layer 112 that is in its normal, non-stretched state and the added elastomeric layer 116 that is under contraction.

Figure 4:
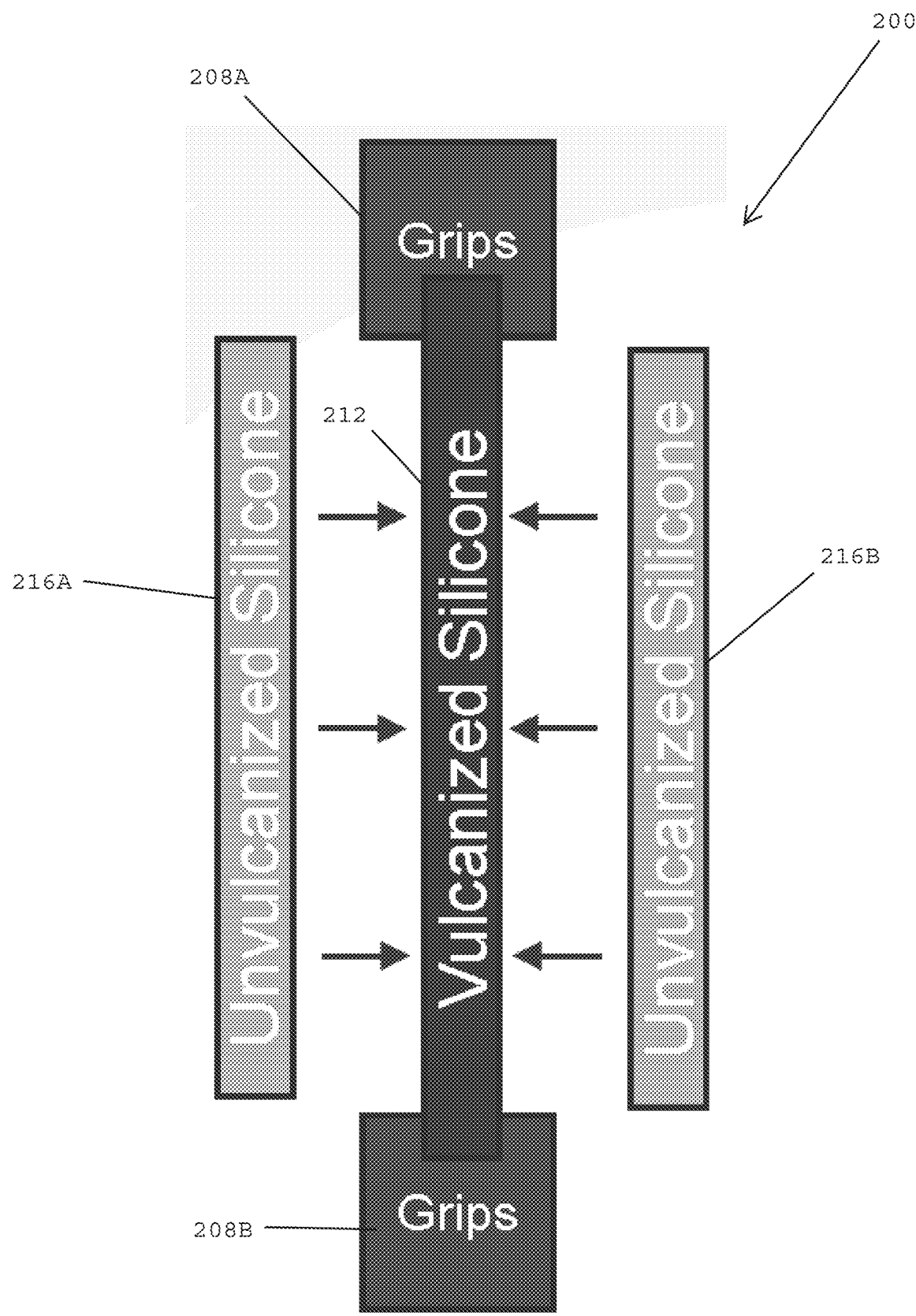
FIG. 4 is a schematic view of a system utilized for making a self-sealing membrane having a three-layer construction with first and second outer zones of the self-sealing membrane being held in contraction by an intermediate zone of the self-sealing membrane, in accordance with one embodiment of the present patent application.

Referring to FIG. 4, in one embodiment, a self-sealing membrane may have a three-layer construction whereby first and second outer layers are held in contraction by an intermediate layer. In one embodiment, a system 200 for making a self-sealing membrane having first and second outer layers held in contraction by an intermediate, middle layer preferably includes two or more grips 208A, 208B that are adapted to grip the outer periphery of a vulcanized silicone sheet 212 for stretching the sheet 212. In one embodiment, a first layer 216A of an unvulcanized polysiloxane elastomer 216A is applied over a first major face of the vulcanized, intermediate layer 212, and a second layer 216B of an unvulcanized polysiloxane elastomer is applied over a second major face of the vulcanized, intermediate layer 212. In one embodiment, while the intermediate layer 212 is stretched by the grips 208A, 208B, the first and second outer layers 216A, 216B are pressed together to form a three-layer construction and the first and second outer layers 216A, 216B are cured by using heat. Once the three-layer construction is fully cured, the grips 208A and 268B may be loosened for releasing the self-sealing membrane from the grips 208A, 208B. Once the self-sealing membrane is released from the grips, the intermediate layer 212 returns to its normal, non-stretched state and the first and second outer layers 216A and 216B are contracted by the intermediate layer 212.

Figure 5A:
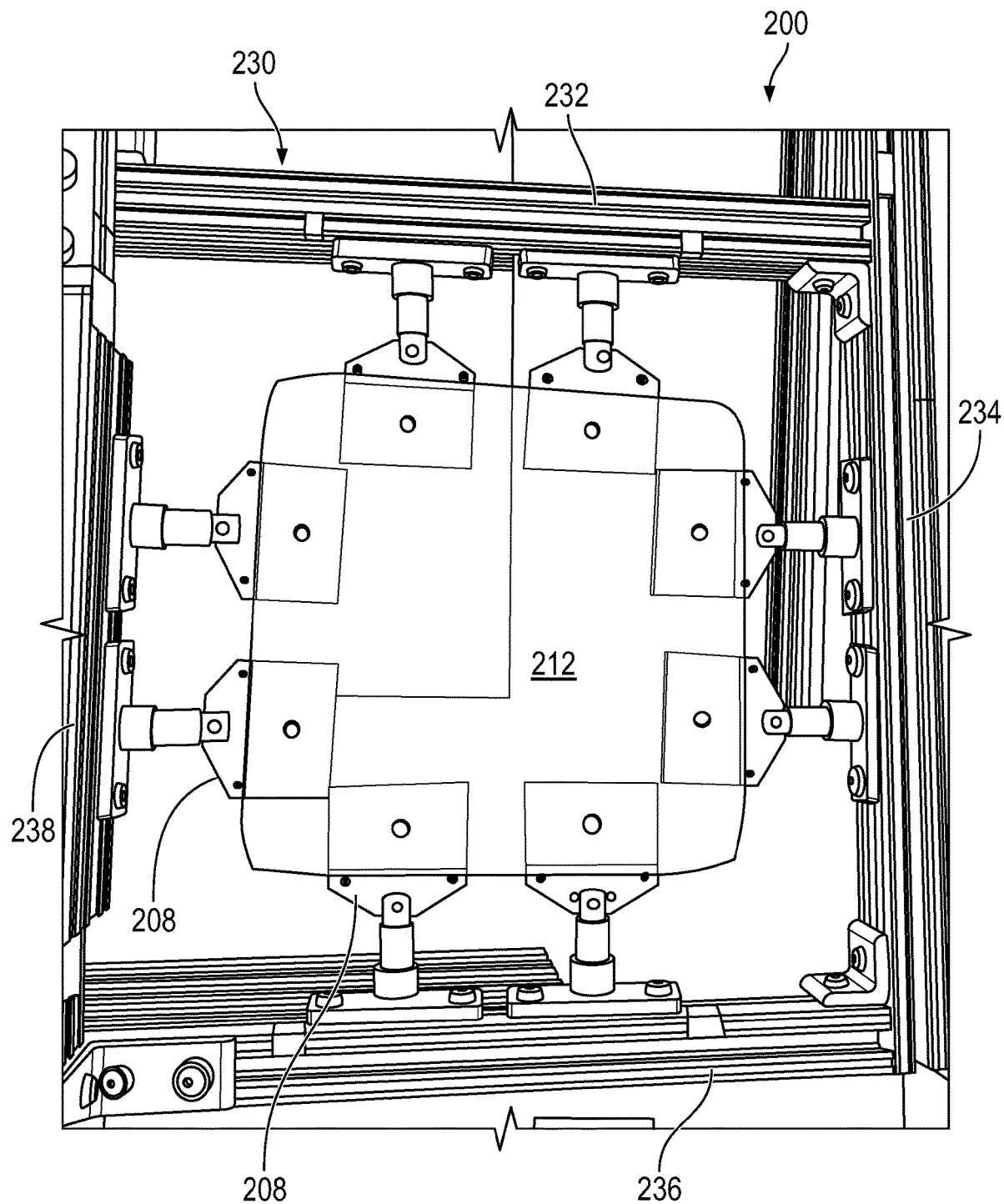
FIG. 5A shows a first step of making a self-sealing membrane having a three-layer construction, in accordance with one embodiment of the present patent application.

Referring to FIG. 5A, in one embodiment, a system 200 for making a self-sealing membrane having three layers preferably includes a frame 230 having four rails 232, 234, 236, and 238 that are adapted to slide relative to one another for selectively modifying the size or area of the frame 230. In one embodiment, each sliding rail preferably supports one or more grips 208 that are adapted to engage the outer perimeter of a vulcanized silicone layer 212. In the particular embodiment shown in FIG. 5A, the system 200 includes a pair of grips 208 attached to each sliding rail 232, 2343, 236, and 238. In one embodiment, the grips 208 desirably project inwardly toward one another from the outer perimeter of the frame 230.

Figure 5B:
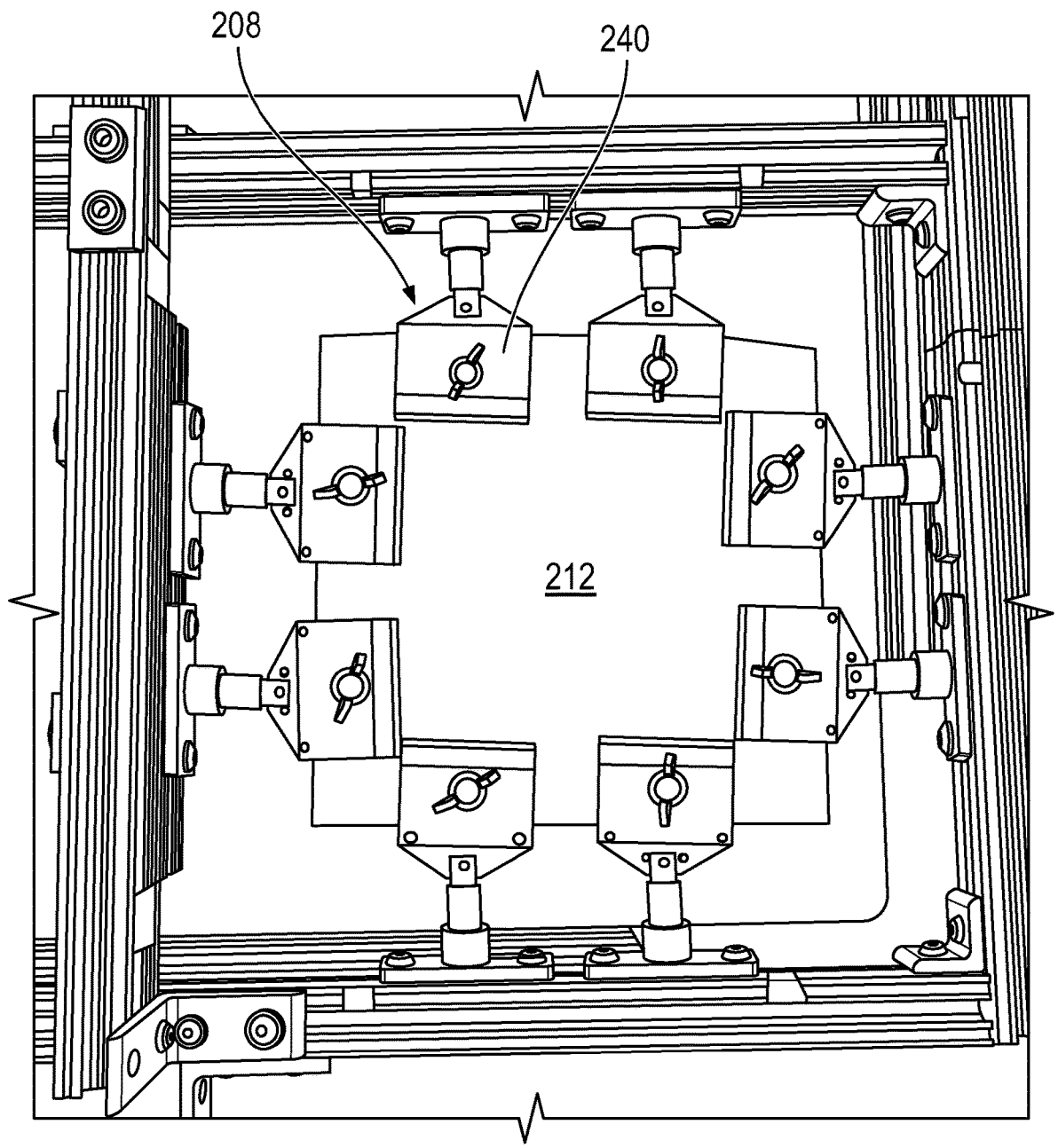
FIG. 5B shows another step of a method of making a self-sealing membrane having a three-layer construction, in accordance with one embodiment of the present patent application.

Referring to FIG. 5B, in one embodiment, the respective grips 208 include clamps 240 that are configured for clamping down onto the outer perimeter (e.g., outer edge) of the vulcanized silicone sheet 212.

Figure 5C:
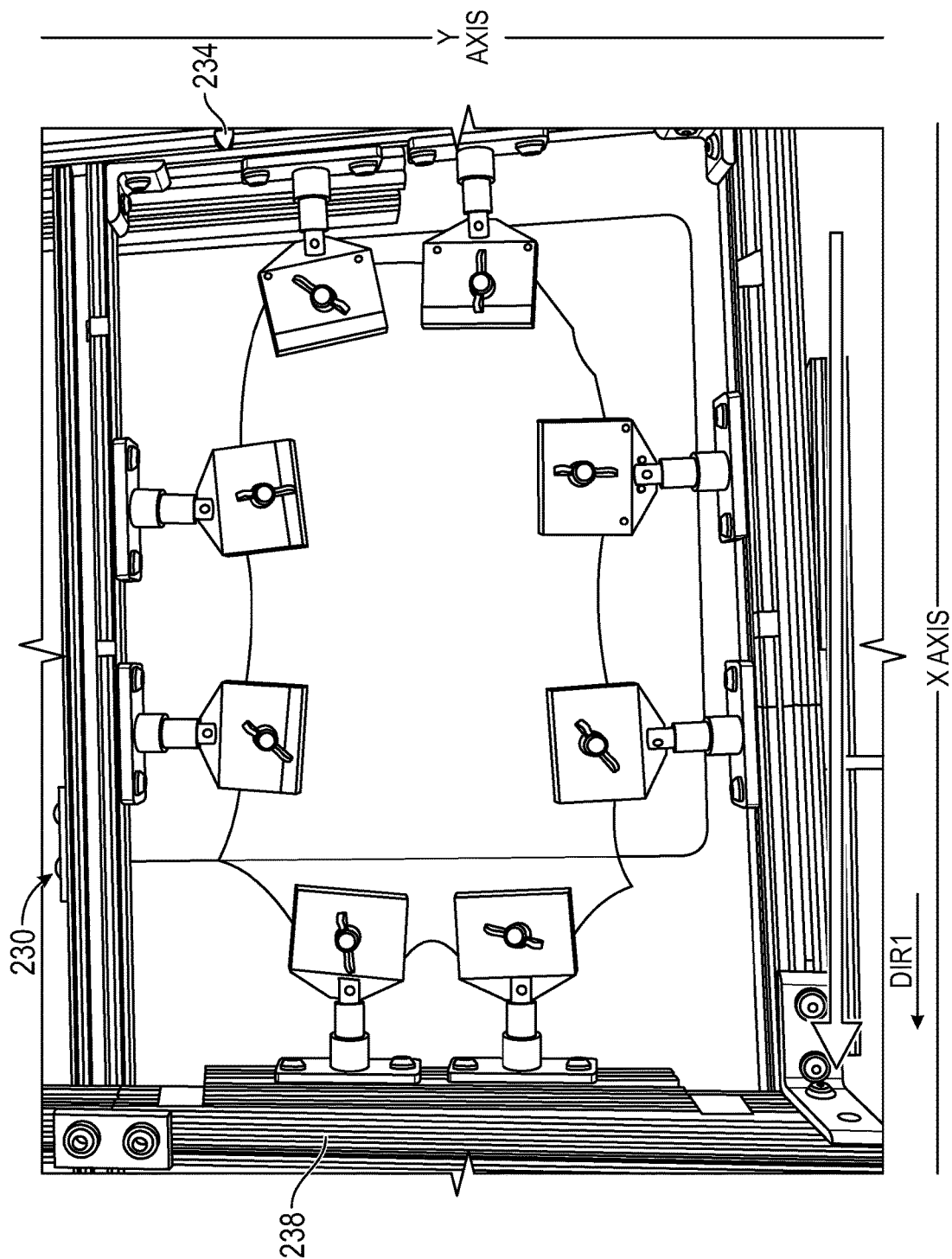
FIG. 5C shows another step of a method of making a self-sealing membrane having a three-layer construction, in accordance with one embodiment of the present patent application.

Referring to FIG. 5C, in one embodiment, the vulcanized silicone sheet 212 has a square or rectangular shape, and the sheet 212 may be stretched within a plane along X and Y axes. In one embodiment, the frame 230 is loosened so that the fourth sliding rail 238 may be moved along the X axis in the direction DIR1 for moving the fourth rail 238 away from the second rail 234 to stretch the vulcanized silicone layer 212 along the X axis. After the fourth rail 238 has been moved into the position shown in FIG. 5C, the frame 230 may be tightened to prevent the rails from shifting along the X axis, thereby maintaining the silicone layer 212 in the stretched configuration shown in FIG. 5C.

Figure 5D:
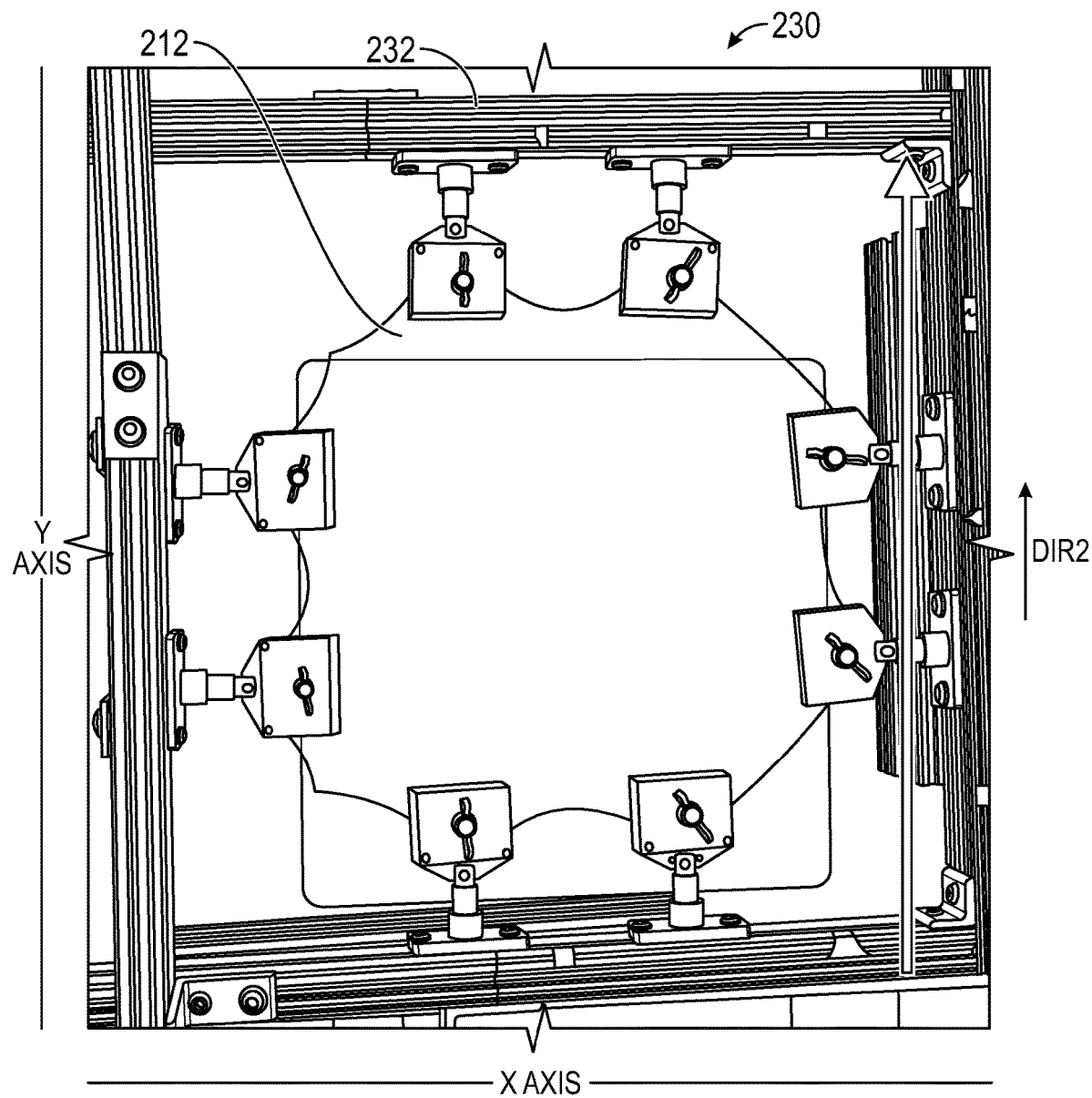
FIG. 5D shows another step of a method of making a self-sealing membrane having a three-layer construction, in accordance with one embodiment of the present patent application.

Referring to FIG. 5D, in one embodiment, the frame 230 may be loosened so that the cured silicone layer 212 may be stretched along the Y axis in the direction DIR2. In one embodiment, the frame 230 is desirably loosened so that the first rail 232 may be slid away from the third rail 236 for stretching the cured silicone layer 212 along the Y axis. The frame 230 may then be tightened to prevent the rails from shifting along the Y axis, thereby maintaining the silicone layer 212 in the stretched configuration shown in FIG. 5D in which the cured silicone layer 212 is stretched along both the X and Y axes. In one embodiment, the frame 230 is desirably loosened so that the rails 232, 234, 236 and 238 can be moved in combination and simultaneously, after which the frame 230 is tightened thereby maintaining the silicone layer 212 in the stretched configuration shown in FIG. 5D, whereby the cured silicone layer 212 is stretched along both the X and Y axes. In one embodiment, the amount of stretching in the X and Y axes is the same to create a uniformly stretched silicone layer 212. In one embodiment, the amount of stretching in the X and Y axes differs to achieve a non-uniform stretched layer having differing self-sealing properties, or different tensile properties along different directions. In one embodiment, rather than using a fixed frame 230, a continuous calendaring process may be used to apply tension to a silicone layer 212, while unvulcanized silicone layers 216A and 216B are applied to the major faces of the silicone layer 212, and subsequently cured through an oven or conveyor belt heating system.

Figure 5E:
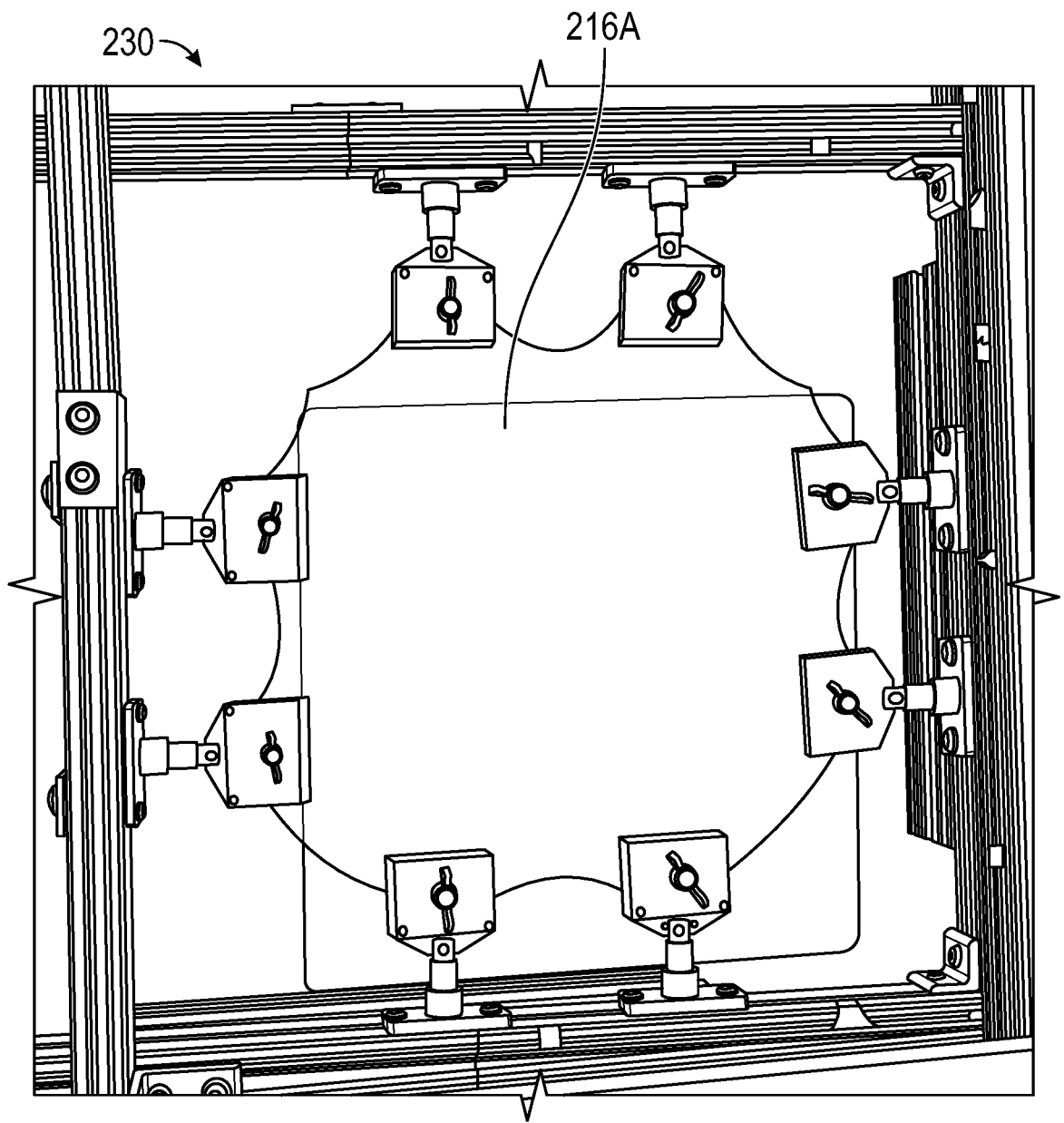
FIG. 5E shows another step of a method of making a self-sealing membrane having a three-layer construction, in accordance with one embodiment of the present patent application.

Referring to FIG. 5E, in one embodiment, a first unvulcanized silicone layer 216A may be applied over a first major surface of the stretched silicone layer 212 (FIG. 5D). The frame 230 may then be reversed to expose a second major surface of the stretched silicone layer. A second unvulcanized silicon layer 216B (FIG. 4) may be applied over the exposed second major surface of the stretched silicone layer 212 (FIG. 5D).

Figure 5F:
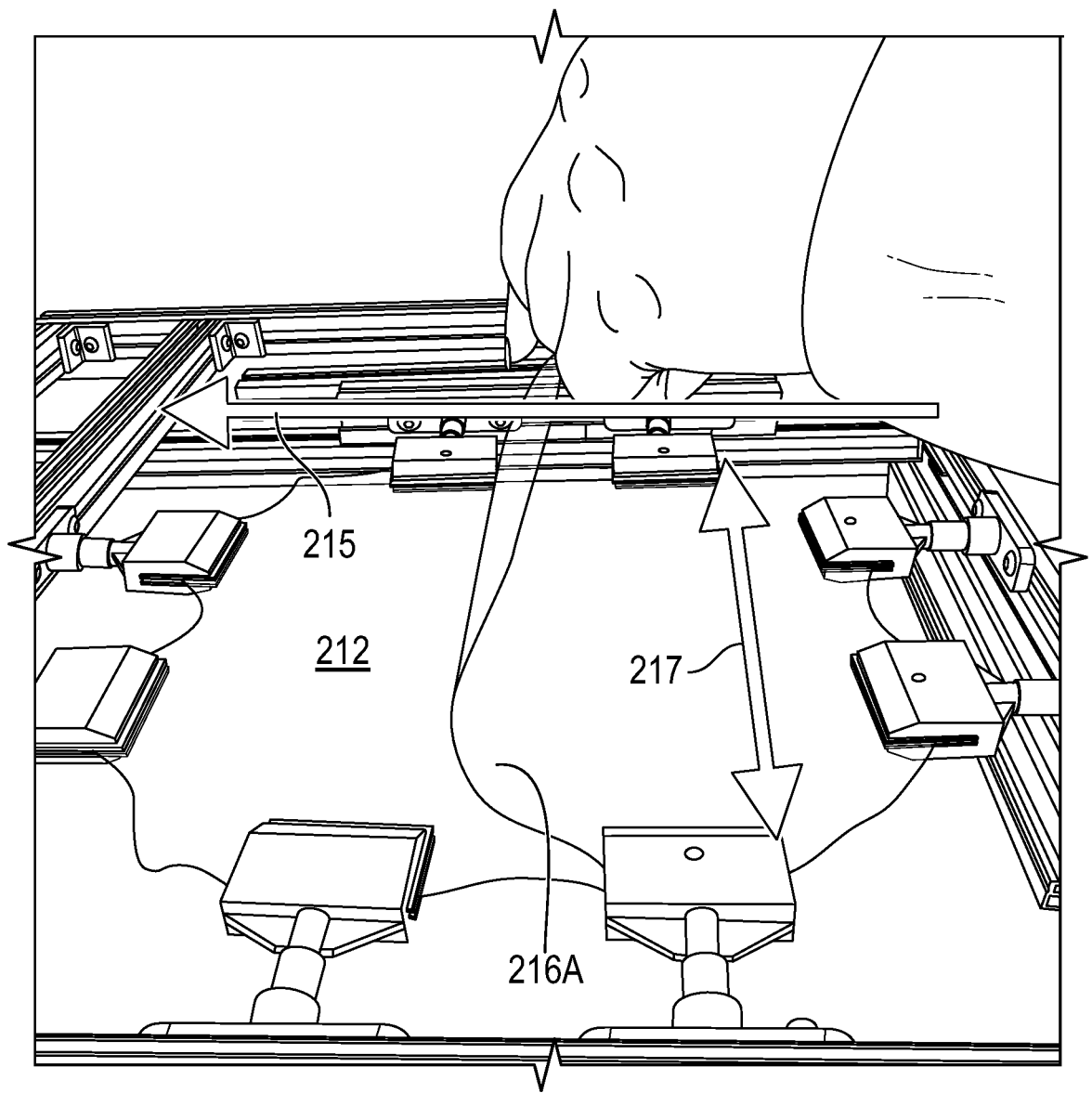
FIG. 5F shows another step of a method of making a self-sealing membrane having a three-layer construction, in accordance with one embodiment of the present patent application.

Referring to FIG. 5F, in one embodiment, the first unvulcanized layer 216A may be applied over a first exposed major surface of the vulcanized layer 212 by gradually laying the first unvulcanized layer 216A onto the exposed, first major surface of the vulcanized layer 212. The unvulcanized layer 216A is applied by gradually laying the layer 216A onto the exposed, first major surface of the vulcanized layer 212 in the direction indicated by the first arrow 215, while concurrently pressing the layer 216A with fingers or blunt tooling aids toward the sides, in the lateral directions indicated by the second arrows 217 to remove air bubbles.

In one embodiment, after the first unvulcanized layer 216A has been applied over the vulcanized layer 212, the frame 230 may be reversed to expose the second major surface of the vulcanized layer, whereupon the second unvulcanized layer 216B may be applied over the second major surface of the vulcanized layer 212.

Figure 5G:
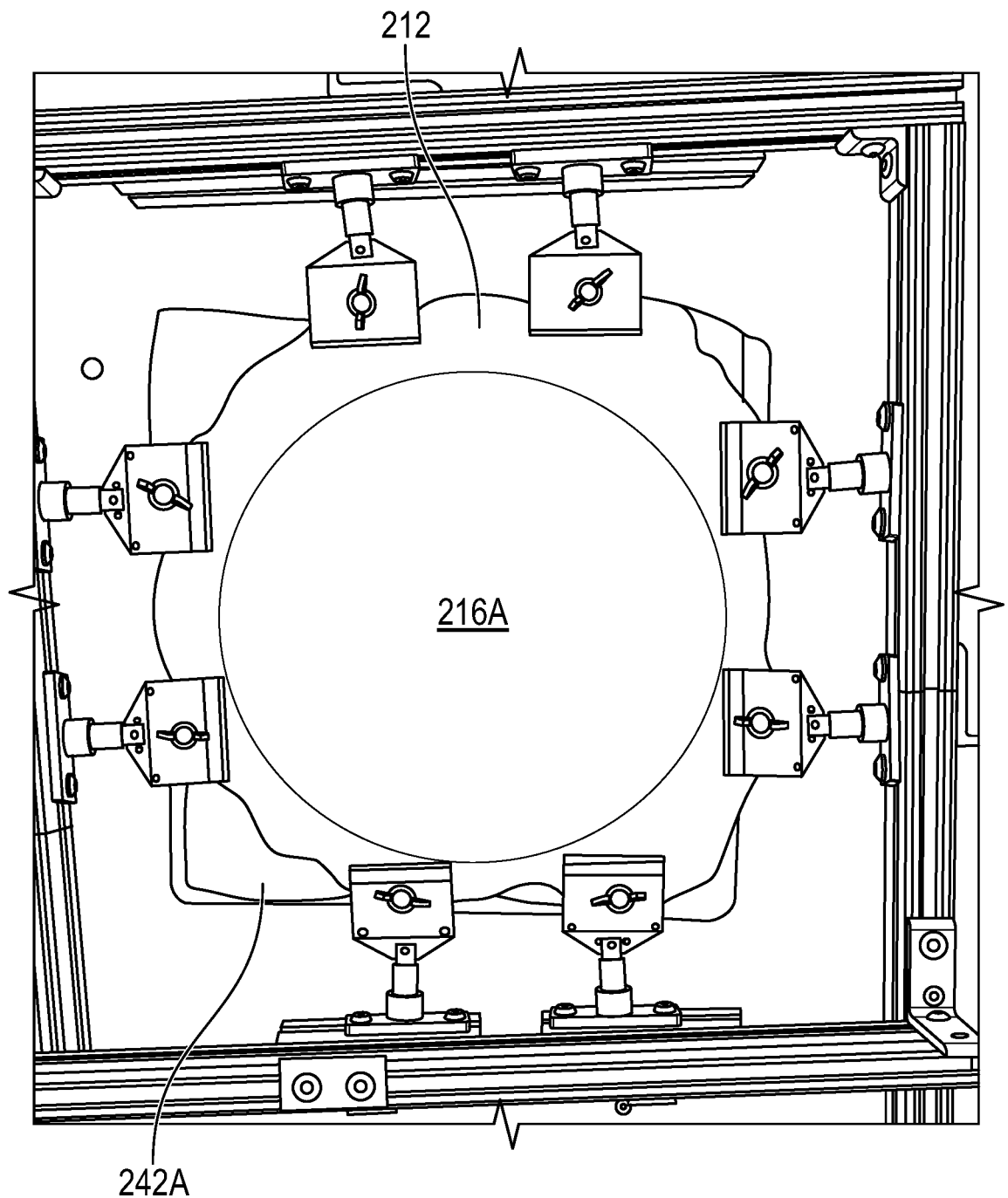
FIG. 5G shows another step of a method of making a self-sealing membrane having a three-layer construction, in accordance with one embodiment of the present patent application.

Referring to FIG. 5G, in one embodiment, a three-layer structure of the stretched vulcanized layer 212 and the two outer unvulcanized layers 216A, 216B may be placed onto a first polyurethane foam layer 242A that underlies the three-layer structure.

Figure 5H:
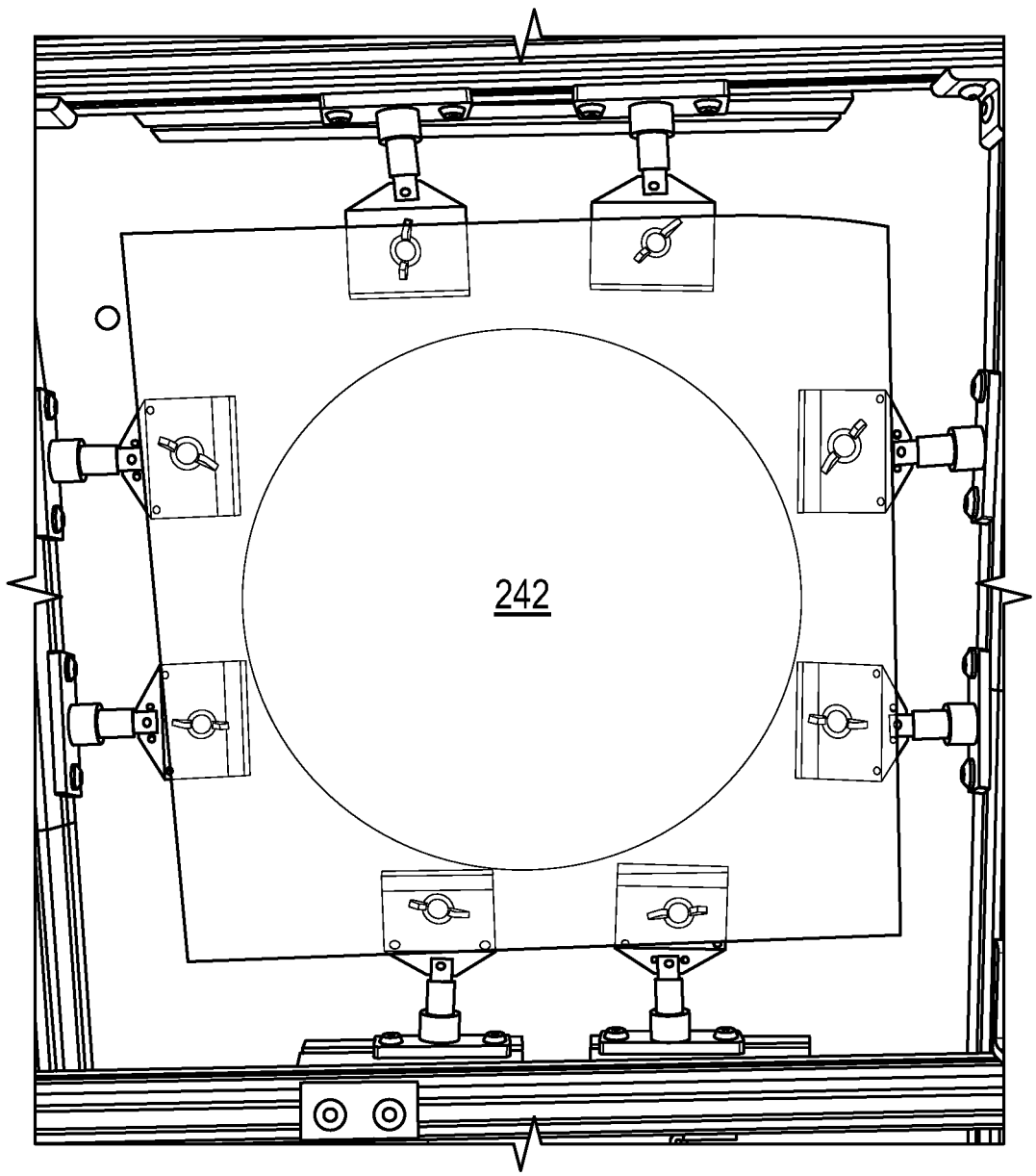
FIG. 5H shows another step of a method of making a self-sealing membrane having a three-layer construction, in accordance with one embodiment of the present patent application.

Referring to FIG. 5H, in one embodiment, a second polyurethane foam layer 242B may be placed on top of the three-layer structure shown in FIG. 5G. In one embodiment, the three-layer structure including the two foam layers 242A (FIG. 5G) and 242B may be placed into a press, such as the press 102 shown and described above in FIG. 1. In one embodiment, the polyurethane foams may be used to apply a desired textured surface to the unvulcanized layers 216A, 216B. In one embodiment, the two polyurethane foams are used as buffering materials to apply more even distribution f compression forces during pressing.

Figure 5I:
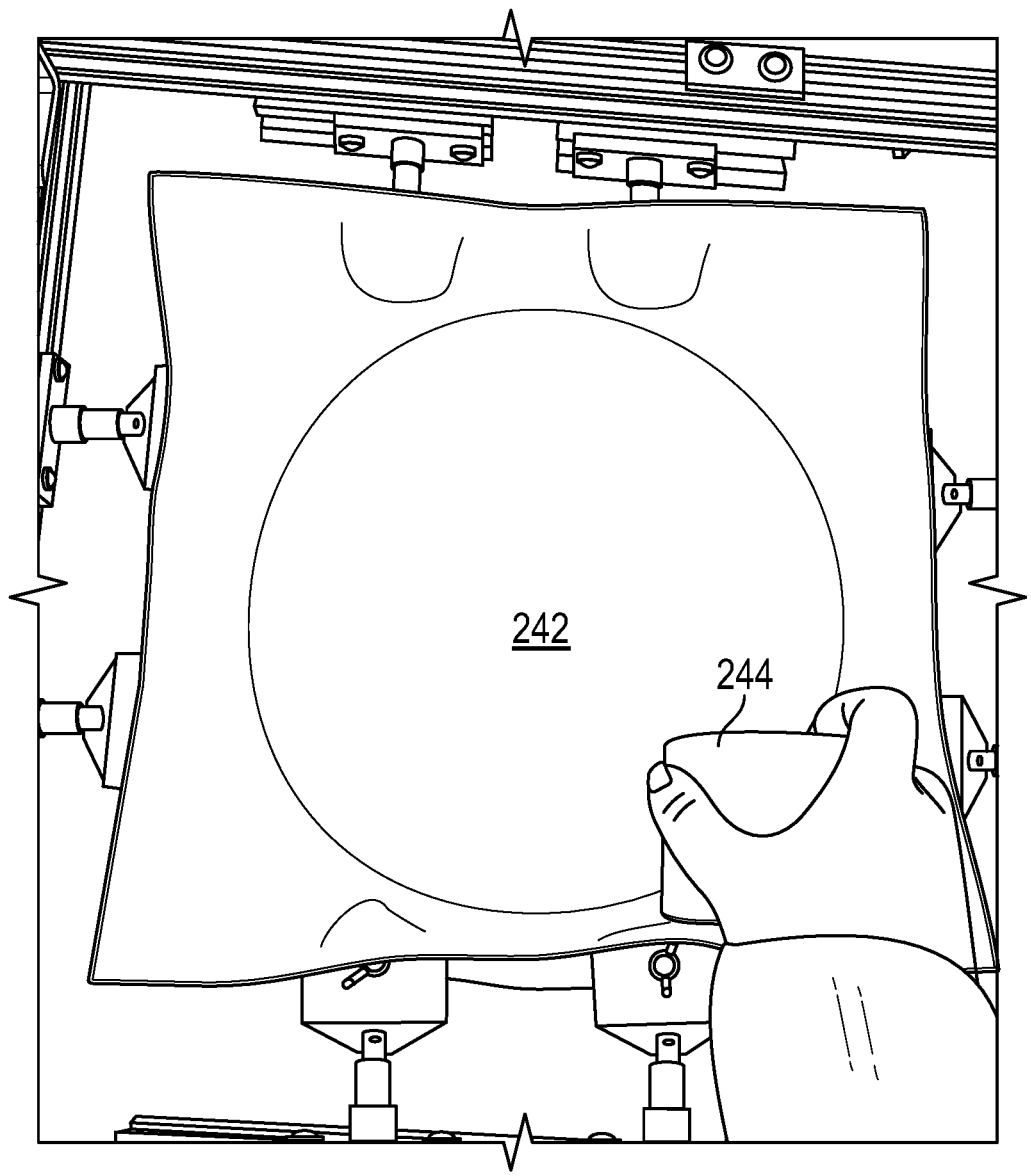
FIG. 5I shows another step of a method of making a self-sealing membrane having a three-layer construction, in accordance with one embodiment of the present patent application.

Referring to FIG. 5I, in one embodiment, a metal roller 244 may be used as a tooling aide for pressing against the foam layers 242A (FIG. 5G) and 242B (FIG. 5H) for compressing the unvulcanized layers 216A, 216B (FIG. 4) onto the stretched silicone layer 212 (FIG. 5F). The platens 104, 106 shown and described above in FIG. 1 may also be used.

Figure 5J:
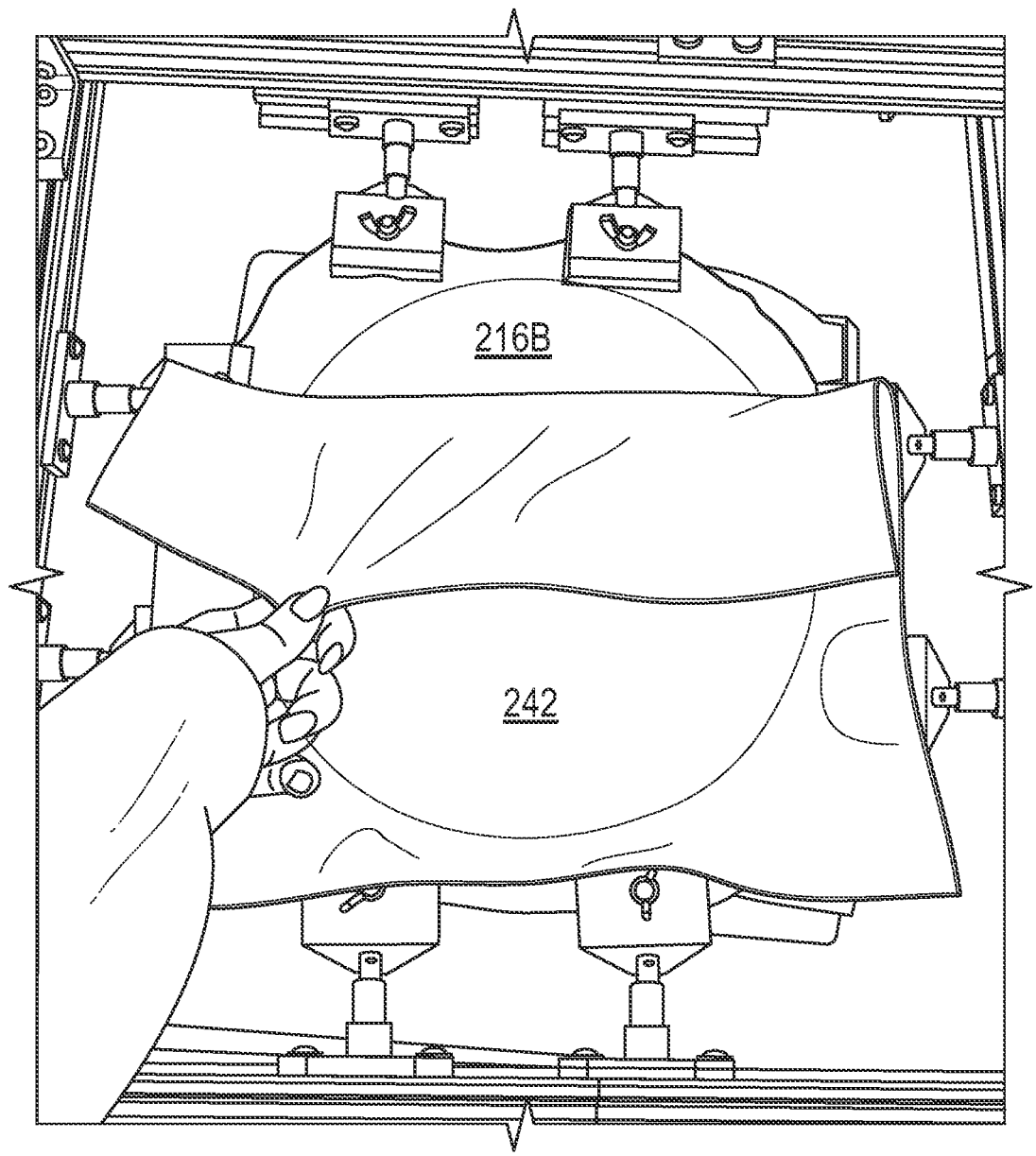
FIG. 5J shows another step of a method of making a self-sealing membrane having a three-layer construction, in accordance with one embodiment of the present patent application.

Referring to FIG. 5J, in one embodiment, after the second foam layer 242B has been pressed into the second unvulcanized layer 216B, the second foam layer 242B may be slowly peeled away to expose the second unvulcanized layer 216B. The frame 230 may be reversed so that the first foam layer 242A may be slowly peeled away to expose the first unvulcanized layer 216A.

Figure 5K:
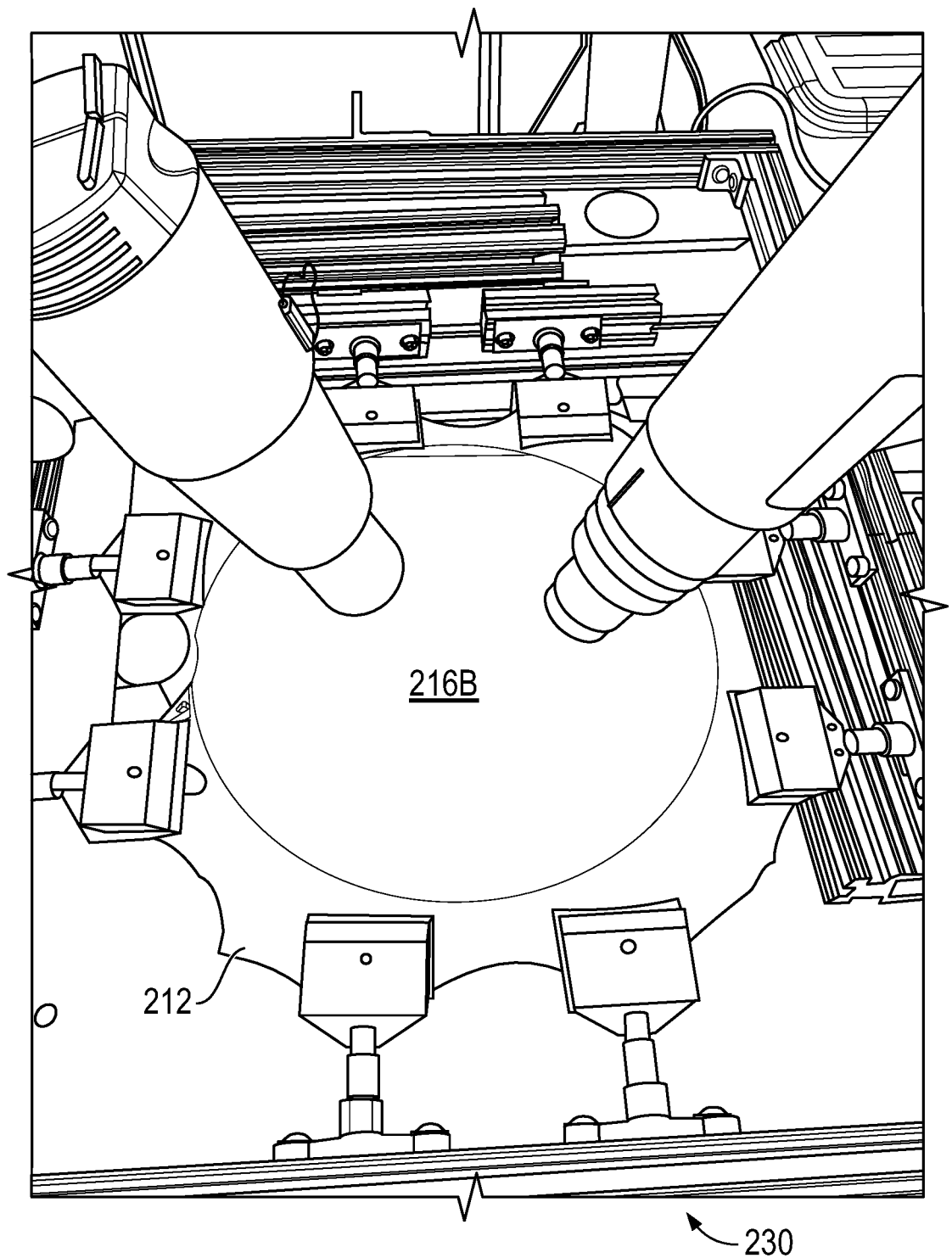
FIG. 5K shows another step of a method of making a self-sealing membrane having a three-layer construction, in accordance with one embodiment of the present patent application.

Referring to FIG. 5K, in one embodiment, the second unvulcanized layer 216B is preferably cured while it remains on the second major surface of the stretched silicone layer 212. In one embodiment, heat guns 250 may be utilized for curing the second unvulcanized layer 216B. In one embodiment, after the second unvulcanized layer 216B has been cured, the frame 230 may be flipped over for curing the first unvulcanized layer 216A that has been applied over the first major surface of the stretched silicone layer 212.

Figure 5L:
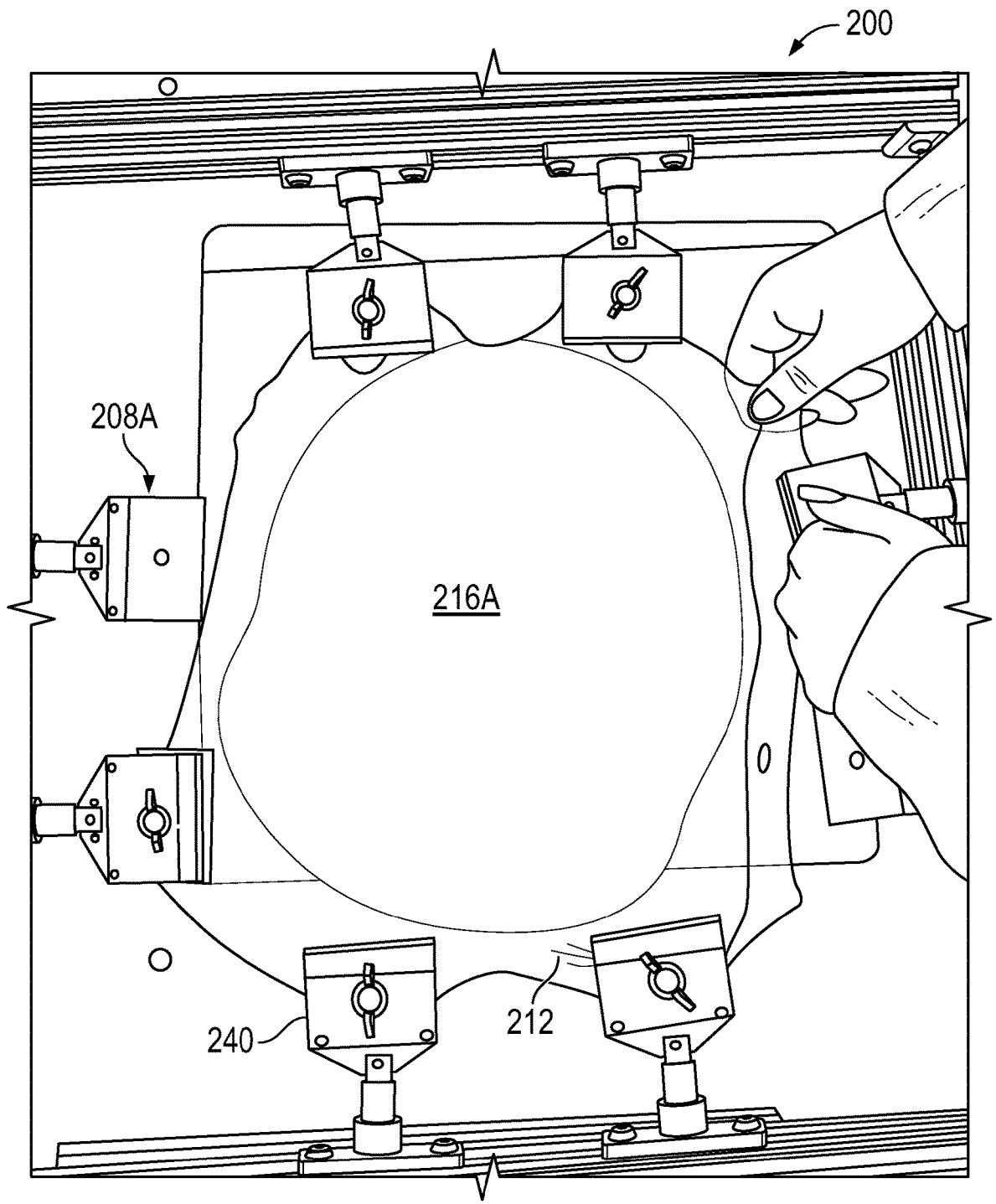
FIG. 5L shows another step of a method of making a self-sealing membrane having a three-layer construction, in accordance with one embodiment of the present patent application.

Referring to FIG. 5L, in one embodiment, after the first and second outer layers 216A and 216B (FIG. 5K) have been cured (e.g., by using heat) over the respective first and second major surfaces of the stretched silicone layer 212, the clamps 240 may be loosened for releasing the outer edges of the silicone sheet 212 from the grips 208 of the system 200.

Figure 6:
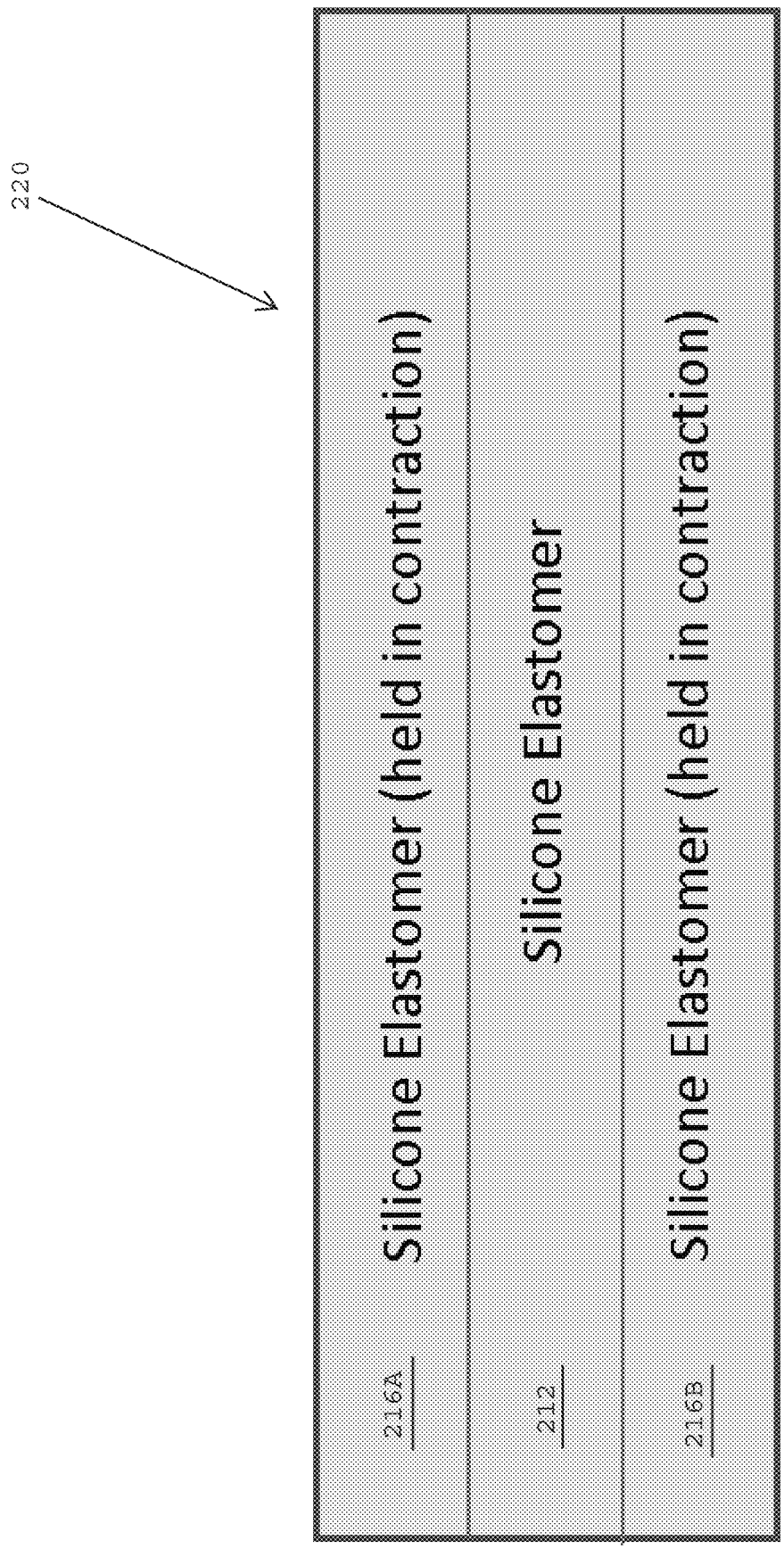
FIG. 6 is a schematic cross-sectional view of a self-sealing membrane for an implant having a three-layer construction including first and second outer zones that are held in contraction by an intermediate zone, in accordance with one embodiment of the present patent application.

Referring to FIG. 6, in one embodiment, the system 200 shown and described above in FIGS. 5A-5L may be utilized for making a self-sealing membrane 220 having three layers including an intermediate layer 212 of a silicone elastomer, and first and second outer layers 216A, 216B of a silicone elastomer that are held in contraction by the intermediate layer 212.

Figure 7A:
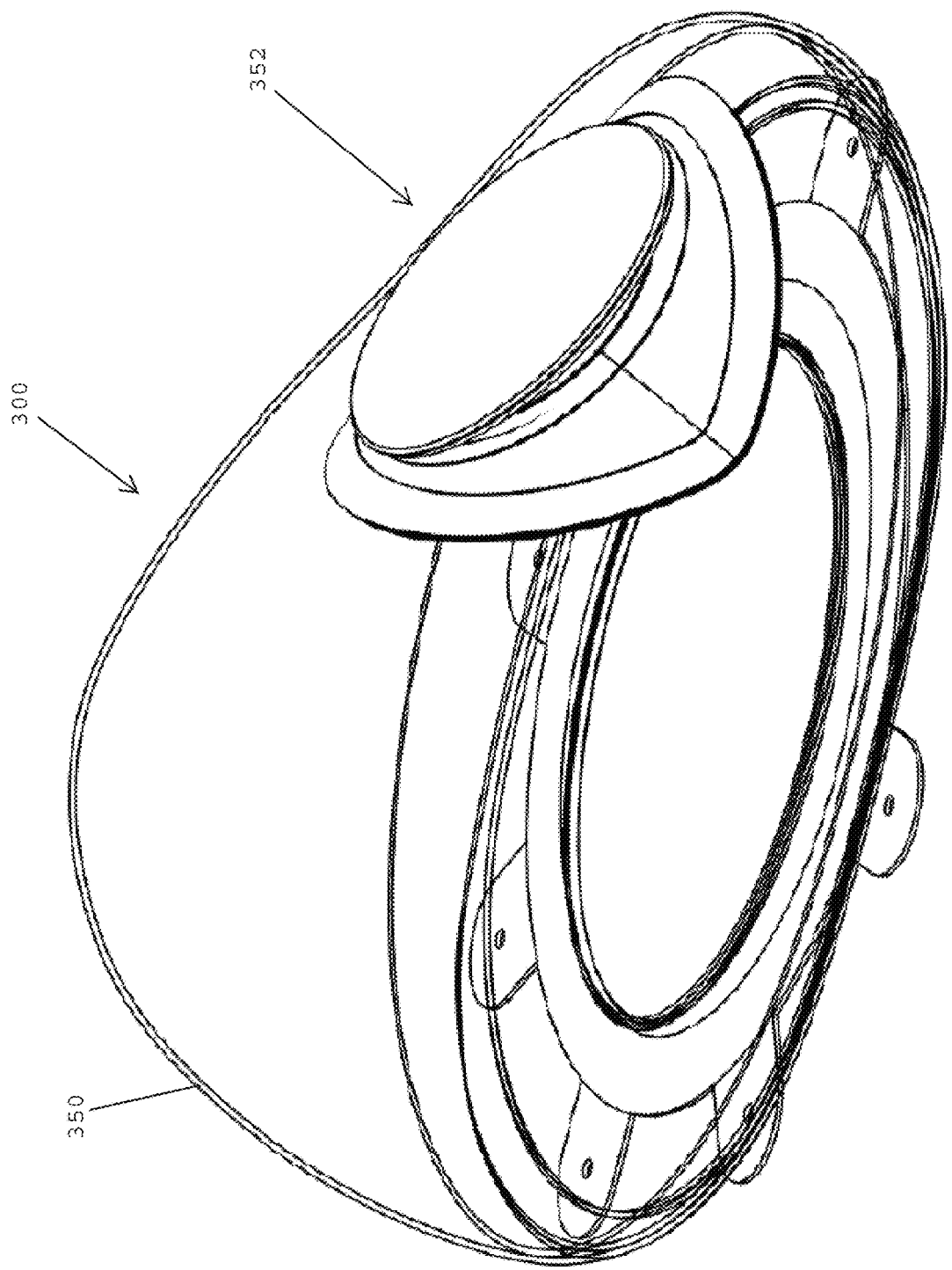
FIG. 7A is a perspective view of a breast tissue expander having an injection port assembly and a self-sealing membrane that surrounds the injection port assembly, in accordance with one embodiment of the present patent application.
Figure 7B:
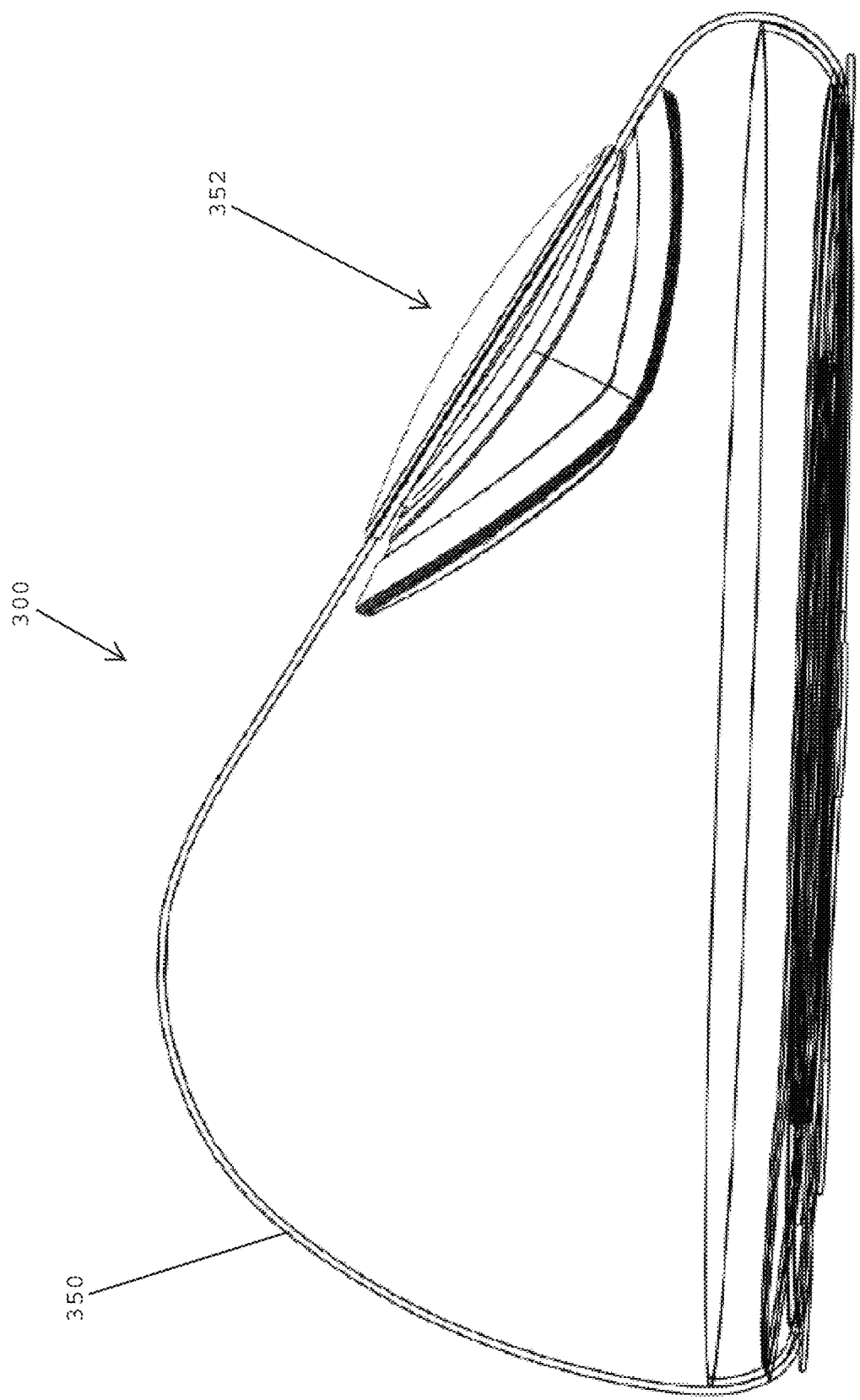
FIG. 7B is a side view of the breast tissue expander shown in FIG. 7A.

Referring to FIGS. 7A and 7B, in one embodiment, a breast tissue expander 300 may be similar to or include one or more of the structural elements disclosed in assigned U.S. Pat. No. 9,700,4040 to Martin et al., assigned to Ethicon, Inc. of Somerville, New Jersey, the disclosure of which is hereby incorporated by reference herein. In one embodiment, the breast tissue expander 300 preferably includes a shell 350 (e.g., a silicone shell) having an injection port assembly 352 with a self-sealing membrane that surrounds the injection port assembly. The self-sealing membrane may be similar to that shown and described above in FIG. 2 or 6.

Figure 8A:
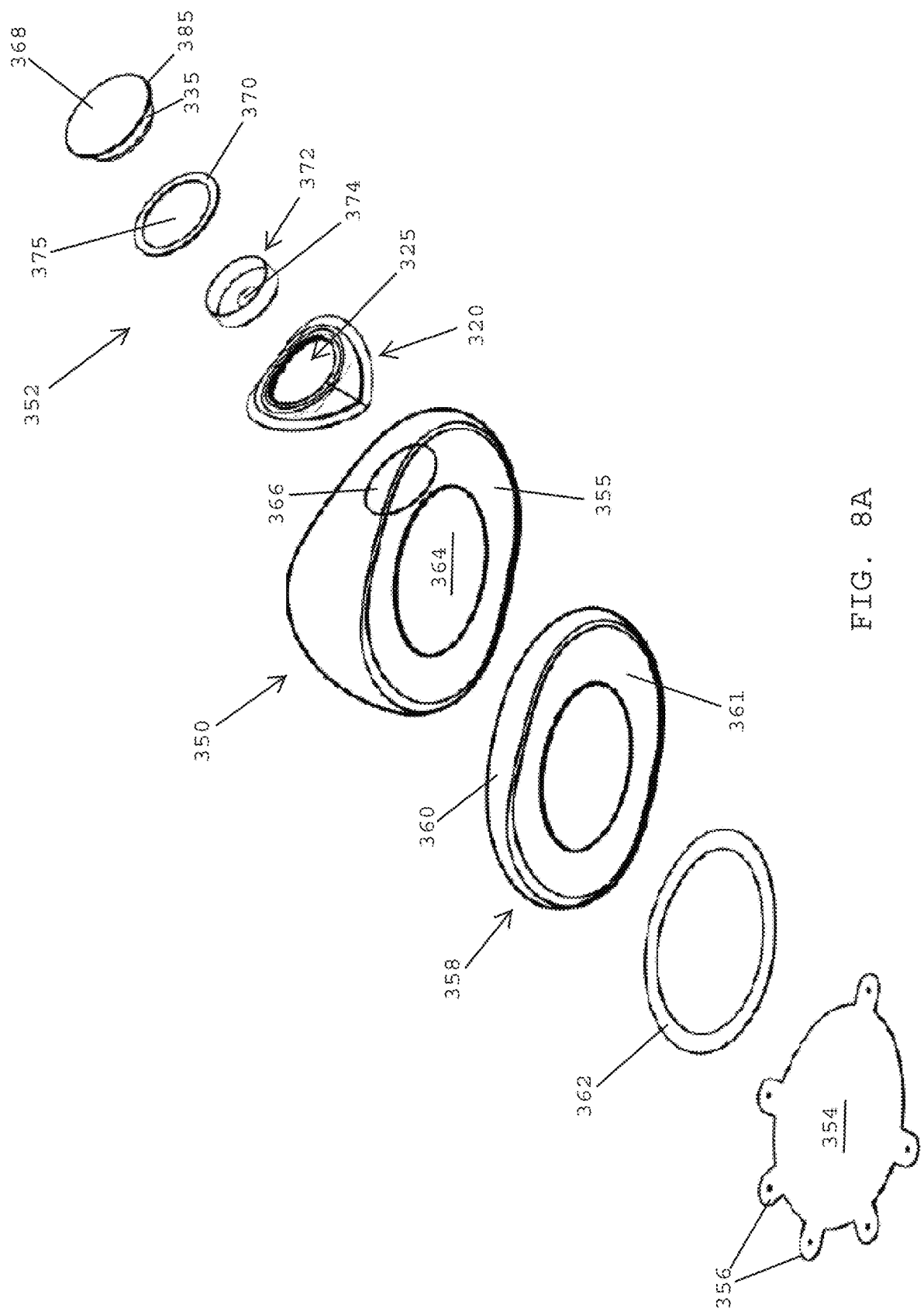
FIG. 8A is an exploded view of the breast tissue expander shown in FIGS. 7A and 7B.
Figure 8B:
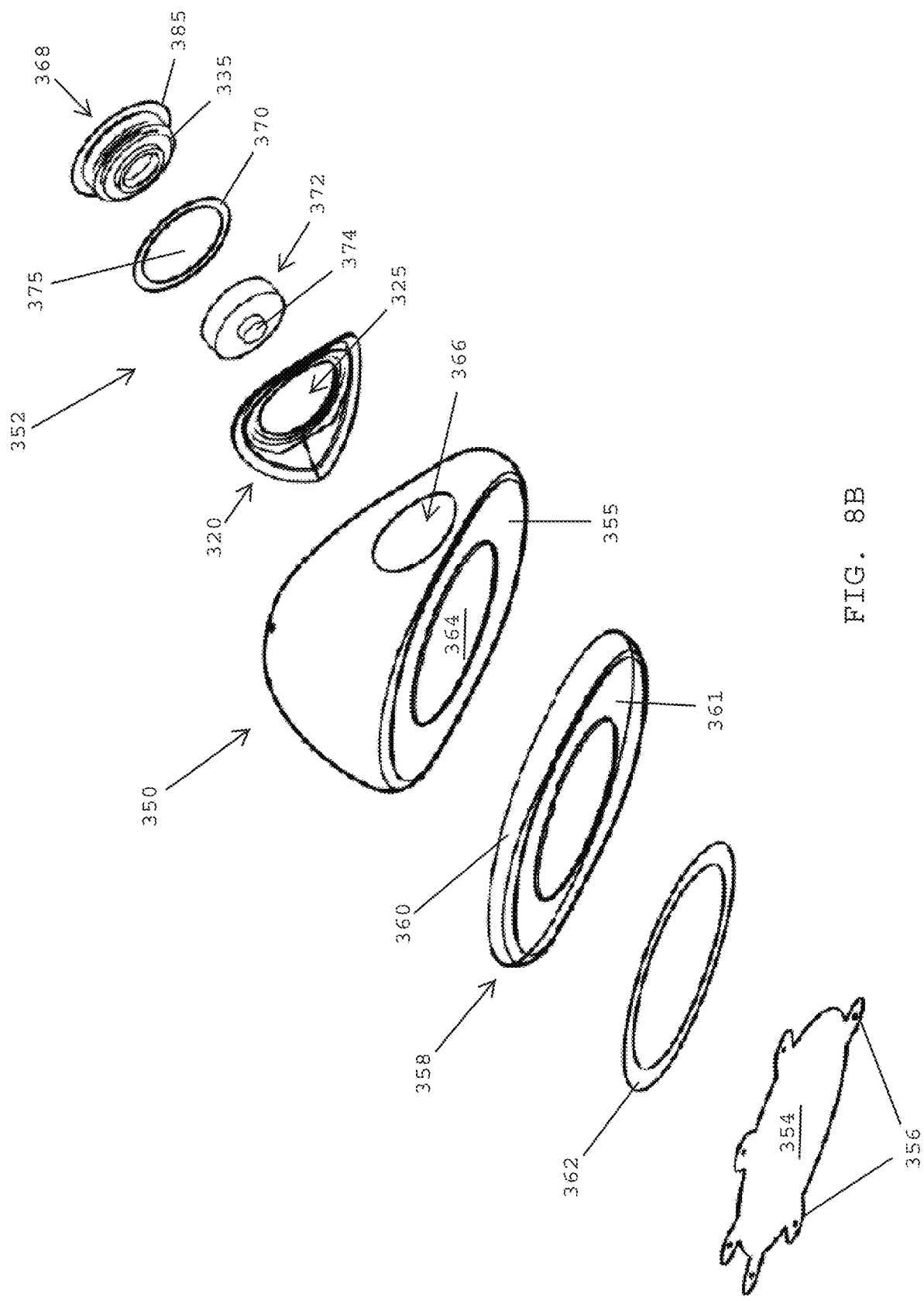
FIG. 8B is another exploded view of the breast tissue expander shown in FIGS. 7A and 7B.

Referring to FIGS. 8A and 8B, in one embodiment, the breast tissue expander 300 preferably includes a base patch 354 having one or more suture tabs 356 that may be utilized for suturing the breast tissue expander 300 to tissue. In one embodiment, the base patch 354 preferably covers a posterior region of the breast tissue expander 300.

In one embodiment, the breast tissue expander 300 preferably includes a self-seal base 358 having a raised rim 360 that is preferably secured to the inside of the shell 350.

In one embodiment, the breast tissue expander 300 preferably includes the shell 350 (e.g., a silicone shell) having a mandrel opening 364 that is covered by the base patch 354, and an injection port opening 366 that is adapted to receive an injection port assembly 352.

In one embodiment, a posterior region of the shell 350 that surrounds the mandrel opening 364 is desirably covered by the self-sealing base 358 to protect the posterior face and the posterior radius of the shell. In one embodiment, the raised rim 360 of the self-sealing base 358 preferably surrounds the posterior radius of the shell 350. In one embodiment, a sealing washer similar to the base patch sealing washer 362 may be utilized for sealing and/or adhering the posterior face 361 of the self-sealing base 358 to the inner surface of the posterior face 355 of the shell 350.

In one embodiment, the injection port assembly 352 preferably includes an injection dome 368 having a port base 335 and a sealing flange 385, an injection dome sealing washer 370 having a central opening 375, a needle guard 372 having a magnet 374, and a self-sealing membrane 320 having a three-layer self-sealing construction as shown and described above in FIG. 6. In one embodiment, the self-sealing membrane 320 desirably has a central opening 325 that is aligned with the injection port opening 366 of the shell 350. In one embodiment, the central opening 325 of the self-sealing membrane 320 is adapted to receive the needle guard 372 and the port base 335 of the injection dome 368.

Referring to FIG. 9, the injection port assembly 352 is preferably adapted to be aligned with the injection port opening 366 of the shell 350. In one embodiment, the self-sealing membrane 320 is preferably disposed inside the shell 350 and is secured to an inner surface of the shell 350 so that the opening 325 of the self-sealing membrane 320 is aligned with the injection port opening 366 of the shell 350. In one embodiment, the needle guard 372 is preferably disposed within the central opening 325 of the self-sealing membrane 320 and the injection port opening 366 of the shell 350.

In one embodiment, injection dome sealing washer 370 is preferably secured to the outer surface of the shell 350 with the central opening 375 of the injection dome sealing washer 370 aligned with the central opening 325 of the self-sealing membrane 320 and the injection port opening 366 of the shell 350.

In one embodiment, after the self-sealing membrane 320 and the injection dome sealing washer 370 have been secured to the shell 350, the shell material that surrounds the injection port opening 366 is preferably sandwiched between the self-sealing membrane 320 and the injection dome sealing washer 370.

In one embodiment, prior to insertion into the central opening 325 of the self-sealing membrane 320, the needle guard 372 and the injection dome 368 are assembled together to form a subassembly. In one embodiment, the injection dome 368 preferably includes the port base 335 and the sealing flange 385 that extends outside the diameter of the port base 335. In one embodiment, when the injection dome 368/needle guard 372 subassembly is assembled with the shell 350, the needle guard 372 and the port base 335 of the injection dome 368 pass through the central opening 375 of the injection dome sealing washer 370 and the central opening 325 of the self-sealing membrane 320, as well as the injection port opening 366 of the shell 350. The sealing flange 385 of the injection dome 368 preferably overlies the outer surface of the shell 350 for engaging the injection dome sealing washer 370, which is also secured to the outer surface of the shell 350.

Figure 10:
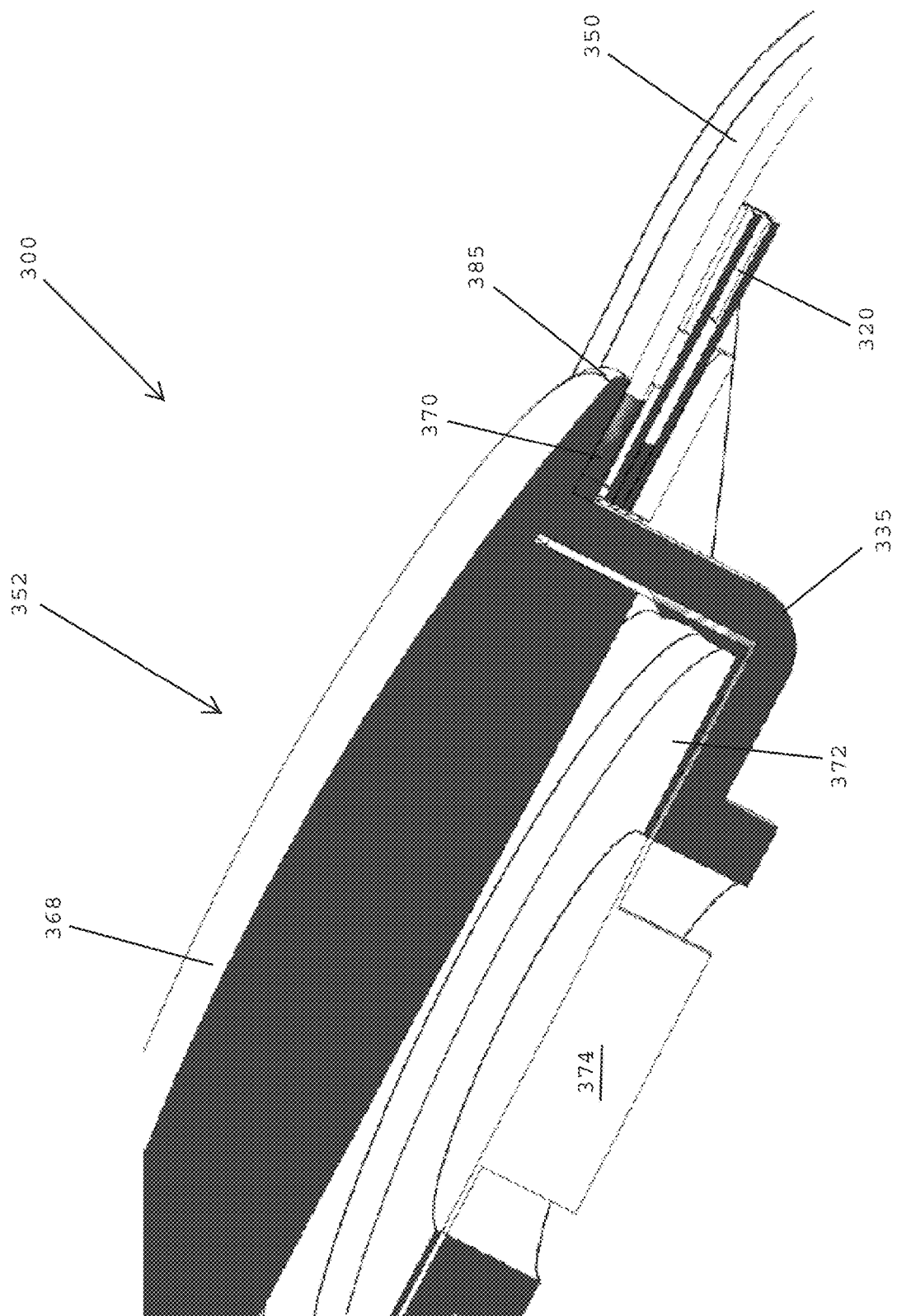
FIG. 10 is a cross-sectional view of a breast tissue expander including a shell, and an injection port assembly that is assembled with the shell, the injection port assembly including an injection dome, an injection dome sealing washer, a needle guard with magnet, and a self-sealing membrane, in accordance with one embodiment of the present patent application.

Referring to FIG. 10, in one embodiment, the injection port assembly 352 is assembled with the shell 350 of the breast tissue expander 300 (FIG. 7A). The injection port assembly 352 preferably passes through the injection port opening 366 (FIG. 8A) of the shell 350. In one embodiment, the self-sealing membrane 320 is secured to the inner surface of the shell 350 and surrounds the injection port opening 366 (FIG. 8A) of the shell 350. The needle guard 372 is assembled with the injection dome 368 so that the needle guard 372 and the port base 335 of the injection dome pass through the central opening 325 (FIG. 8A) of the self-sealing membrane 320 as well as the injection port opening 366 (FIG. 8A) of the shell 350. The magnet 374 is secured to an underside of the needle guard 372. The sealing flange 385 of the injection dome 368 extends outwardly beyond the outer perimeter of the injection port opening 366 (FIG. 8A) of the shell 350. The injection dome sealing washer 370 preferably secures an underside of the sealing flange 385 of the injection dome 368 to an outer surface of the shell 350.

Figure 11A:
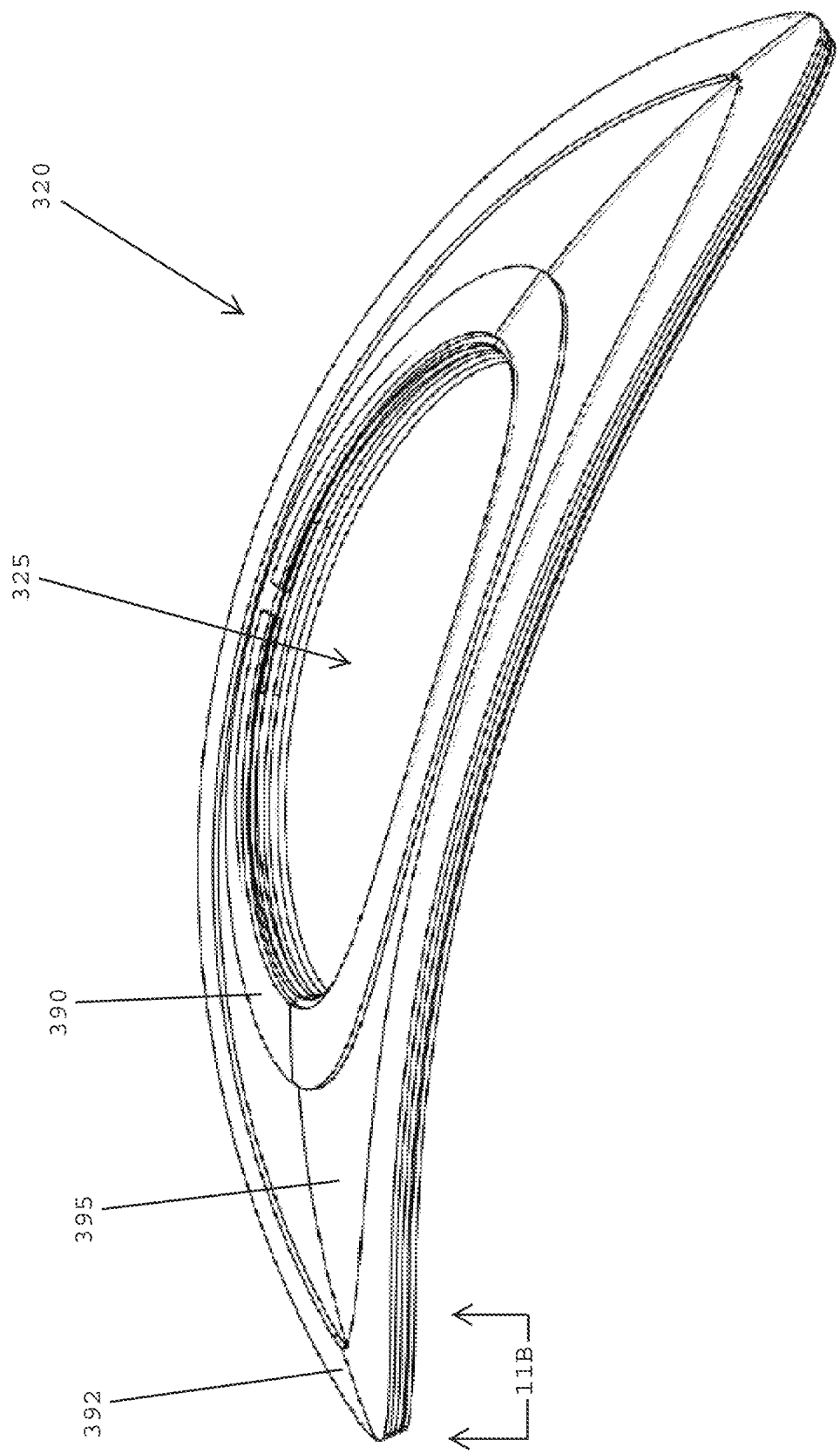
FIG. 11A is a perspective view of a top side of the self-sealing membrane shown in FIG. 9.

Referring to FIG. 11A, in one embodiment, the self-sealing membrane 320 preferably includes the three-layer construction shown and described above in FIG. 6. In one embodiment, the self-sealing membrane preferably has the central opening 325 that is adapted to receive a needle guard and a base of an injection dome. As described above, the central opening 325 is preferably aligned with an injection port opening 366 (FIG. 8A) formed in a shell of a breast tissue expander. In one embodiment, the self-sealing membrane 320 preferably includes an inner washer 390 that surrounds the central opening 325 and an outer washer 392 that extends around the outer perimeter of the self-sealing membrane 320. In one embodiment, the inner and outer washers 390, 392 are preferably utilized for securing a top surface 395 of the self-sealing membrane 322 to an inner surface of a shell of a mammary implant. In one embodiment, the first and second sealing washers 390, 392 may be replaced by a single washer that extends outwardly between the outer perimeter of the central opening 325 and the outer perimeter of the self-sealing membrane, and that completely covers the top surface 395 of the self-sealing membrane 320.

Figure 11B:
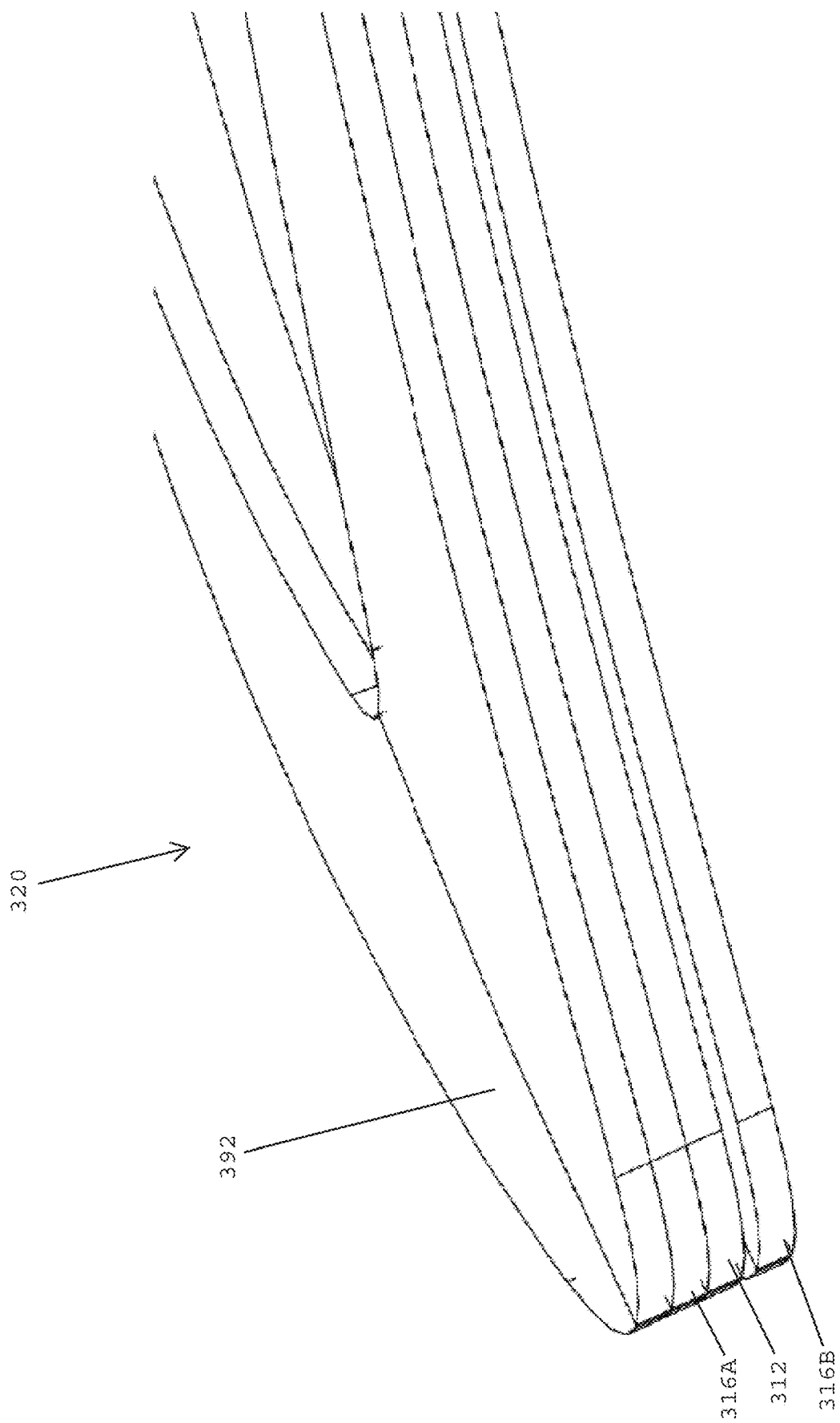
FIG. 11B is a magnified view of an outer edge of the self-sealing membrane shown in FIG. 11A.

Referring to FIG. 11B, in one embodiment, the self-sealing membrane 320 preferably includes a three-layer construction having an intermediate layer 312 that is sandwiched between first and second outer layers 316A and 316B. The first and second outer layers 316A and 316B are preferably held in contraction by the intermediate layer 312. The outer sealing washer 392 preferably overlies the outer perimeter of the first outer layer 316A for securing the anterior face of the self-sealing membrane 320 to an inner surface of a shell of a breast tissue expander.

Figure 12A:
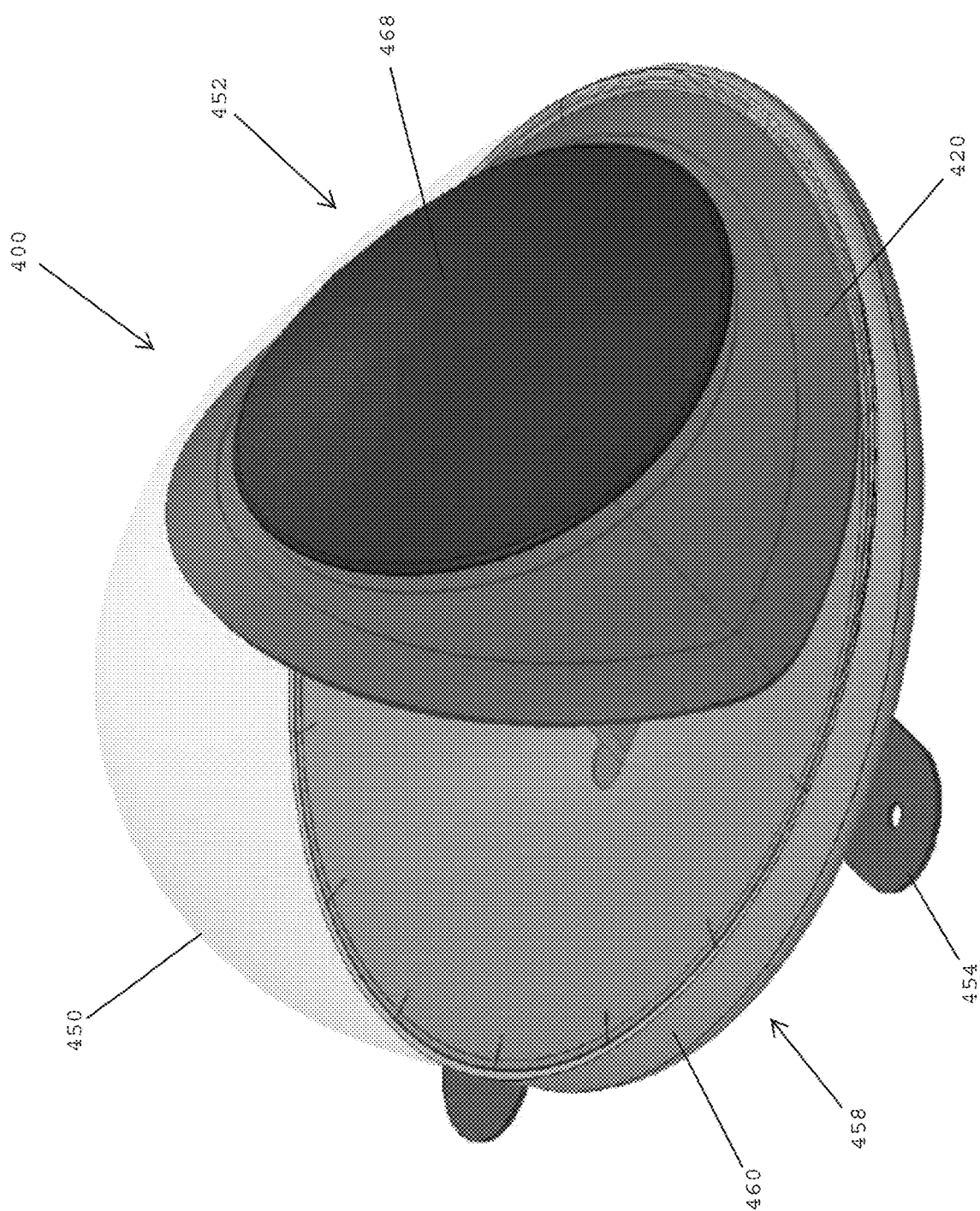
FIG. 12A is a perspective view of a breast tissue expander including a shell having an anterior region with a first self-sealing membrane that surrounds an injection port assembly, and a posterior region with a second self-sealing membrane that surrounds a base and radius of the posterior region, in accordance with one embodiment of the present patent application.

Referring to FIGS. 12A and 12B, in one embodiment, a breast tissue expander 400 may be similar to or include one or more of the structural elements disclosed in U.S. Pat. No. 9,463,087 to Hristov et al., assigned to Mentor Worldwide LLC, of Irvine, California, the disclosure of which is hereby incorporated by reference herein. In one embodiment, the breast tissue expander 400 preferably includes a shell 450 with an injection port assembly 452 assembled around an injection port opening of the shell 450. In one embodiment, the breast tissue expander 400 preferably includes a self-sealing membrane 420 as shown and described herein that surrounds an injection dome 468 of the injection port assembly 452.

In one embodiment, the breast tissue expander 400 includes a seal-sealing base 458 having a raised rim 460 that extends between a posterior region of the shell 450 and a base patch 454. In one embodiment, the self-sealing base 458 preferably includes the self-sealing structure disclosed herein for minimizing the risk of a leak if the self-sealing base 458 is punctured during a suturing operation.

Figure 13:
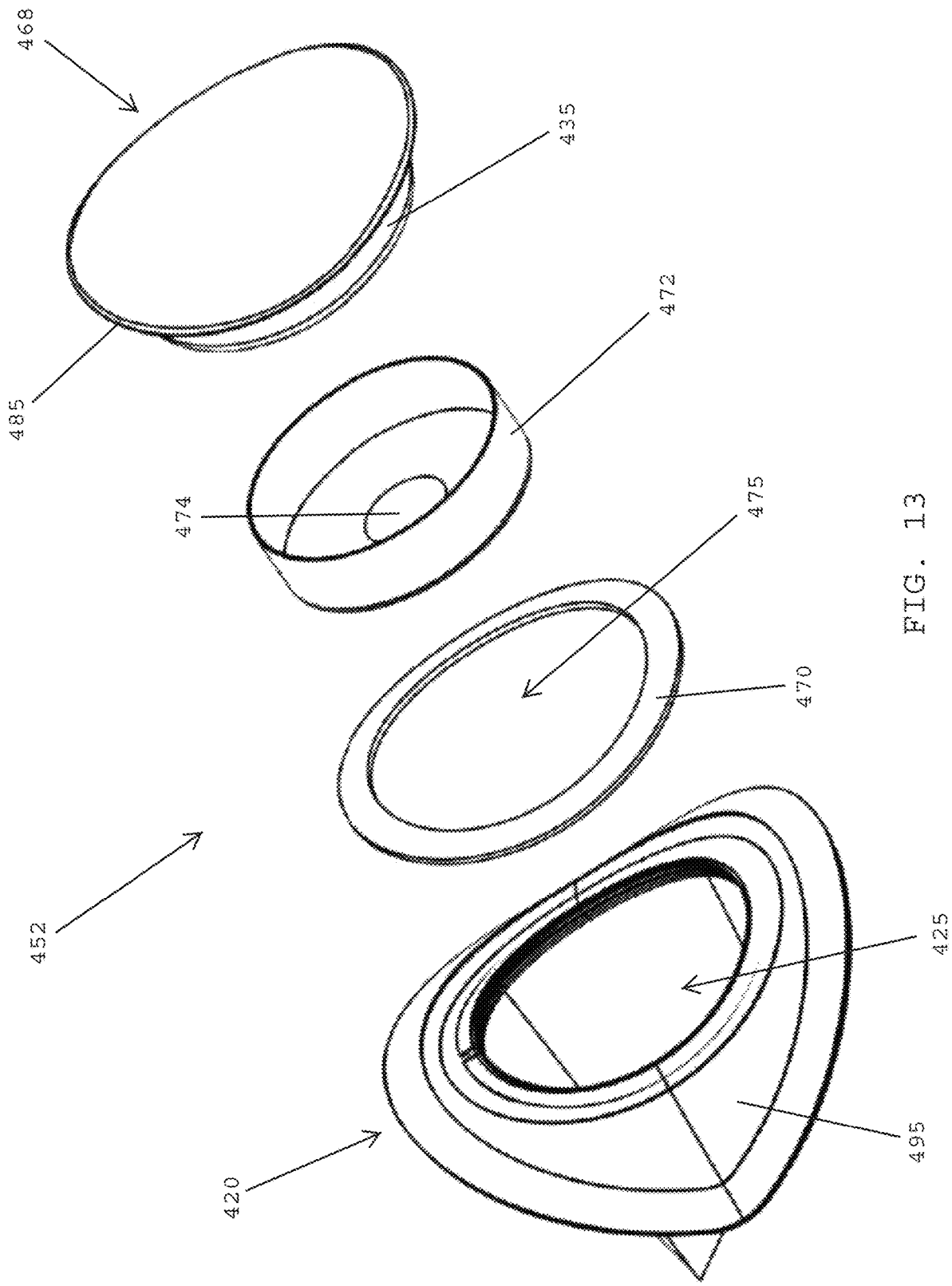
FIG. 13 is an exploded view of the injection port assembly of the breast tissue expander shown in FIGS. 12A and 12B including an injection dome, a needle guard with magnet, an injection dome sealing washer, and a self-sealing membrane that surrounds the injection dome, in accordance with one embodiment of the present patent application.

Referring to FIG. 13, in one embodiment, the injection port assembly 452 of the breast tissue expander 400 shown and described above in FIGS. 12A and 12B preferably includes a self-sealing membrane 420 having a central opening 425, a needle guard 472 having a magnet 474, an injection dome 468 having a base 435 and a sealing flange 485, and an injection dome sealing washer 470 having a central opening 475 that is adapted to receive the needle guard 472 and the base 435 of the injection dome 468.

In one embodiment, when the self-sealing membrane 420 is assembled with an inner surface of a shell of a breast tissue expander, the anterior face 495 of the self-sealing membrane 420 is desirably secured to the inner surface of the shell. The injection dome sealing washer 470 is preferably secured to an outer surface of the shell and surrounds the central opening 425 of the self-sealing membrane 420. The needle guard 472 passes through the central opening 475 of the injection dome sealing washer 470 and the central opening 425 of the self-sealing membrane 420. The injection dome 468 is assembled with the shell by abutting a posterior face of the injection dome sealing flange 485 with the anterior face of the injection dome sealing washer 470, whereupon the injection dome sealing flange 485 of the injection dome 468 overlies the outer surface of the shell of the breast tissue expander.

Figure 14A:
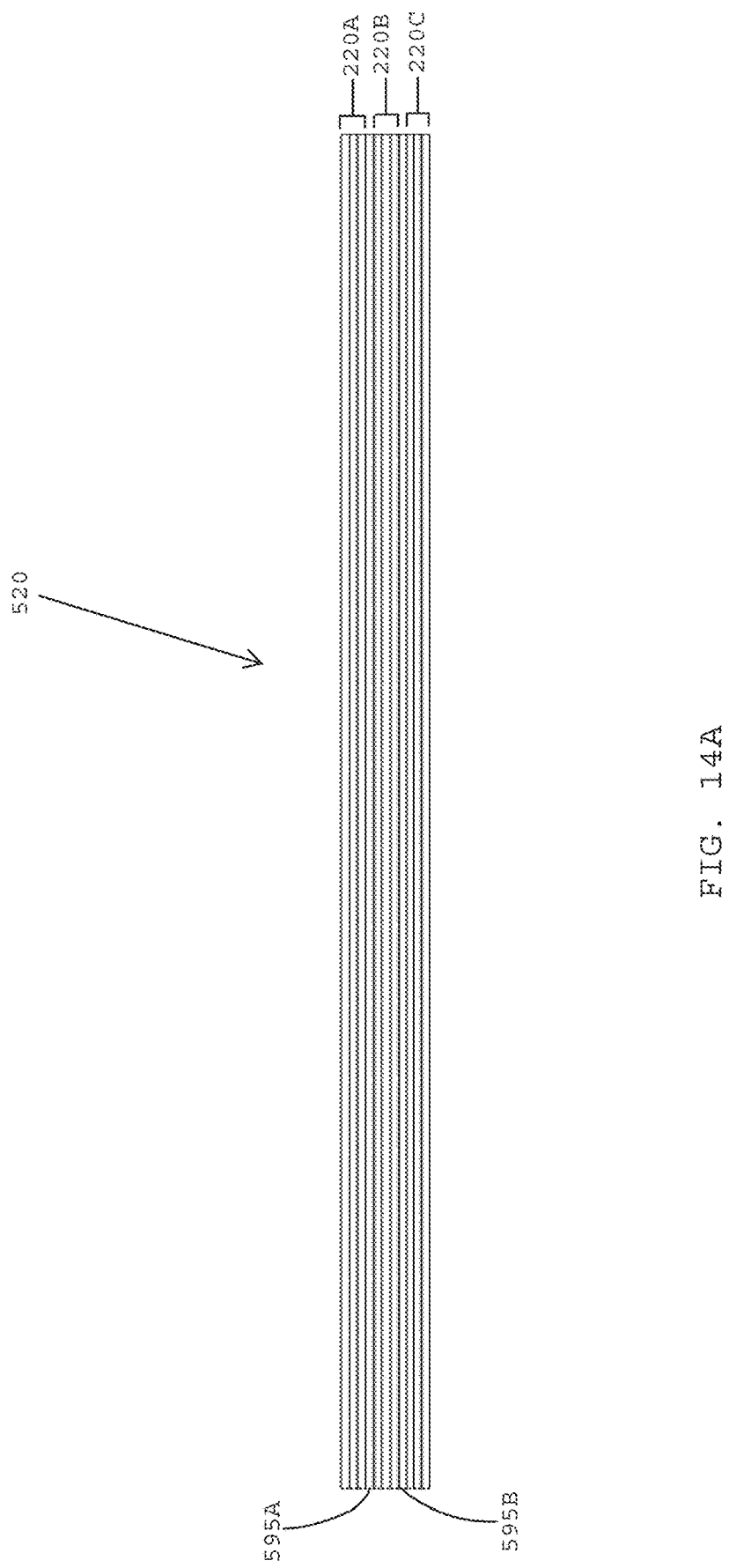
FIG. 14A is a side view of a self-sealing sheet for an injection port assembly, the self-sealing sheet including a plurality of self-sealing membranes that are joined together, each self-sealing membrane having a three-layer construction with first and second outer zones held in contraction by an intermediate zone, in accordance with one embodiment of the present patent application.

Referring to FIG. 14A, in one embodiment, a self-sealing sheet 520 for an implant may include two or more of the three-layer self-sealing membranes 220 shown and described above in FIG. 6. In one embodiment, the self-sealing sheet 520 preferably includes three different self-sealing membranes 220A, 220B, and 220O that are joined together by unvulcanized sealing layers 595A and 595B that may be cured for adhering the three self-sealing membranes 220A, 220B, and 220C to one another.

Figure 14B:
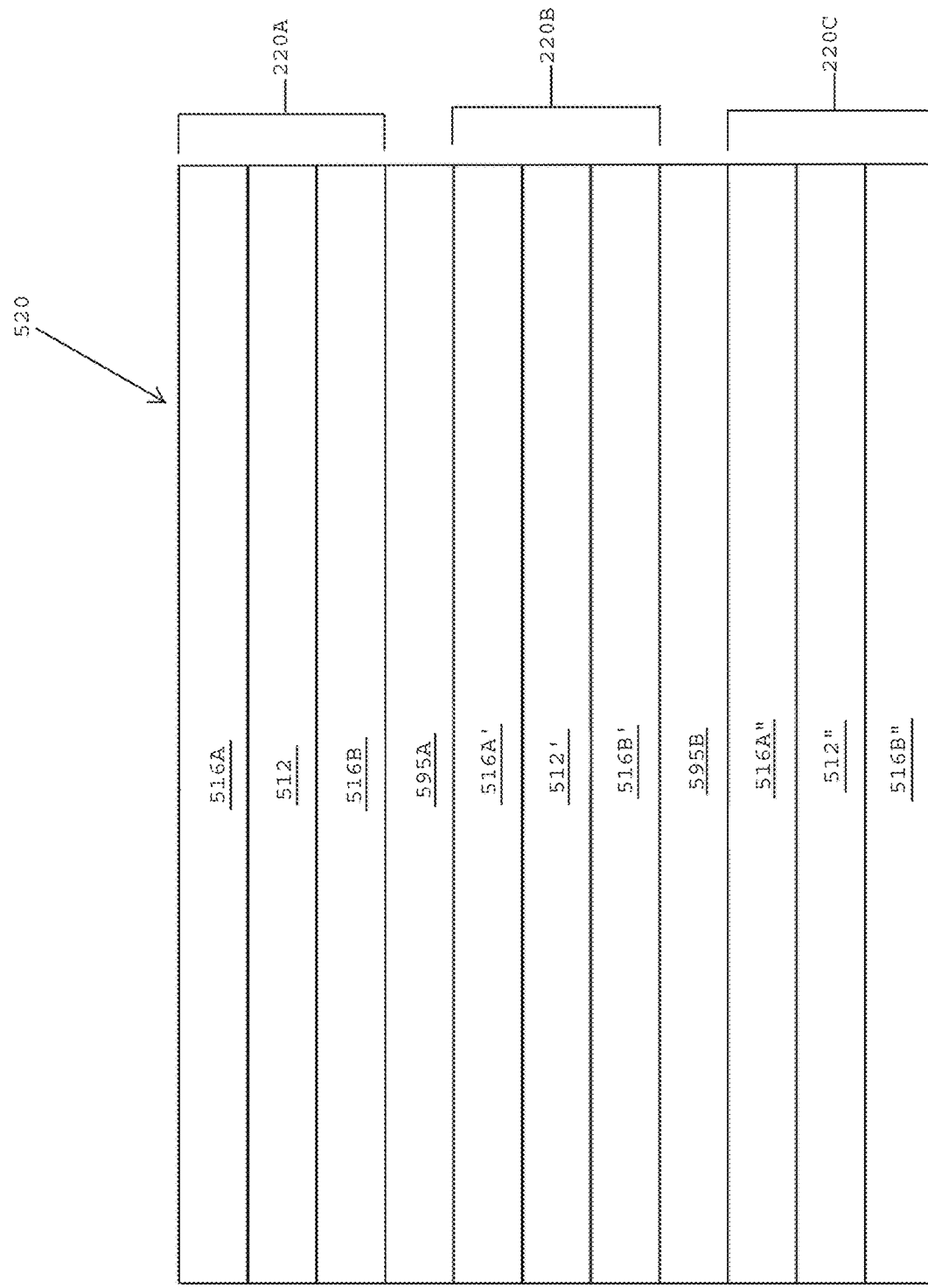
FIG. 14B is a magnified view of a section of the self-sealing sheet shown in FIG. 14A.

Referring to FIG. 14B, in one embodiment, the self-sealing sheet 520 preferably includes a first self-sealing membrane 220A having first and second outer layers 516A and 516B that are held in contraction by an intermediate layer 512. The self-sealing sheet 520 preferably includes a second self-sealing membrane 220B including first and second outer layers 516A' and 516B' that are held in contraction by intermediate layer 512'. In one embodiment, the seal-sealing sheet 520 preferably includes a third self-sealing membrane having first and second outer layers 516A" and 516B" that are held in contraction by intermediate layer 512". In one embodiment, the first and second self-sealing members 220A and 220B are joined together by an unvulcanized layer 595A that may be cured. In one embodiment, the second third self-sealing membranes 220B and 220C are joined together by a second unvulcanized layer 595B that may be cured.

In one embodiment, the self-sealing sheet 520 shown in FIGS. 14A and 14B may be incorporated anywhere on a mammary implant to close needle openings after the self-sealing sheet 520 has been punctured by a needle. In one embodiment, unvulcanized layers 595 are not required and a plurality of alternating layers of 120 may be constructed by stacking multiple alternating layers of cured silicone shells 112 and unvulcanized layers 116 (FIG. 1). In one embodiment, unvulcanized layers 595 are not required and a plurality of alternating layers of 120 may be constructed by stacking multiple alternating layers of cured silicone shells 112 and unvulcanized layers 116 as in the process shown in FIG. 1, or by stretching multiple layers of vulcanized silicone sheets 212 with alternating layers of unvulcanized silicone 216 as in the process shown in FIG. 4.

Figure 15A:
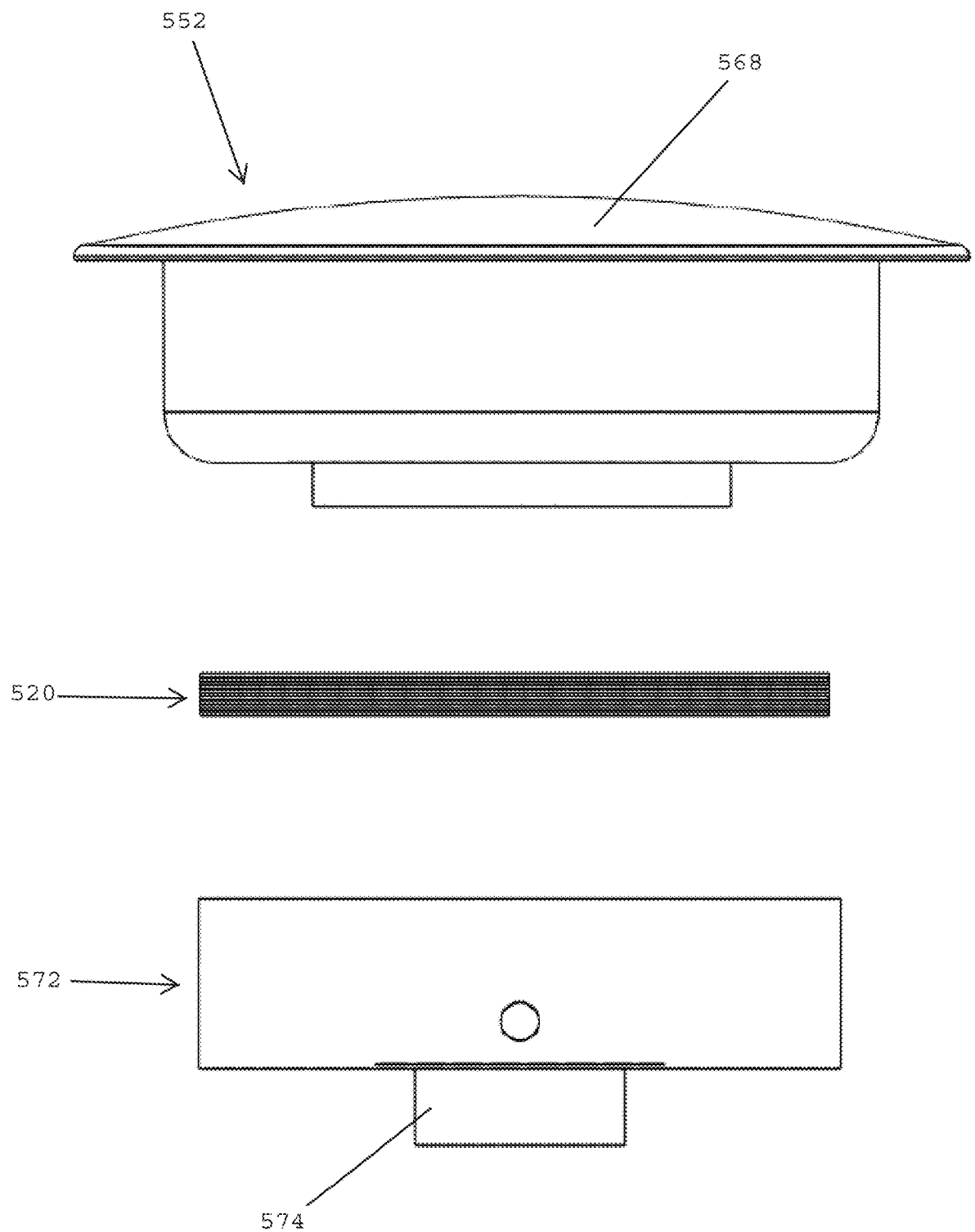
FIG. 15A is an exploded view of an injection port assembly for a breast tissue expander including an injection dome, a self-sealing sheet, and a needle guard with magnet, in accordance with one embodiment of the present patent application.
Figure 15B:
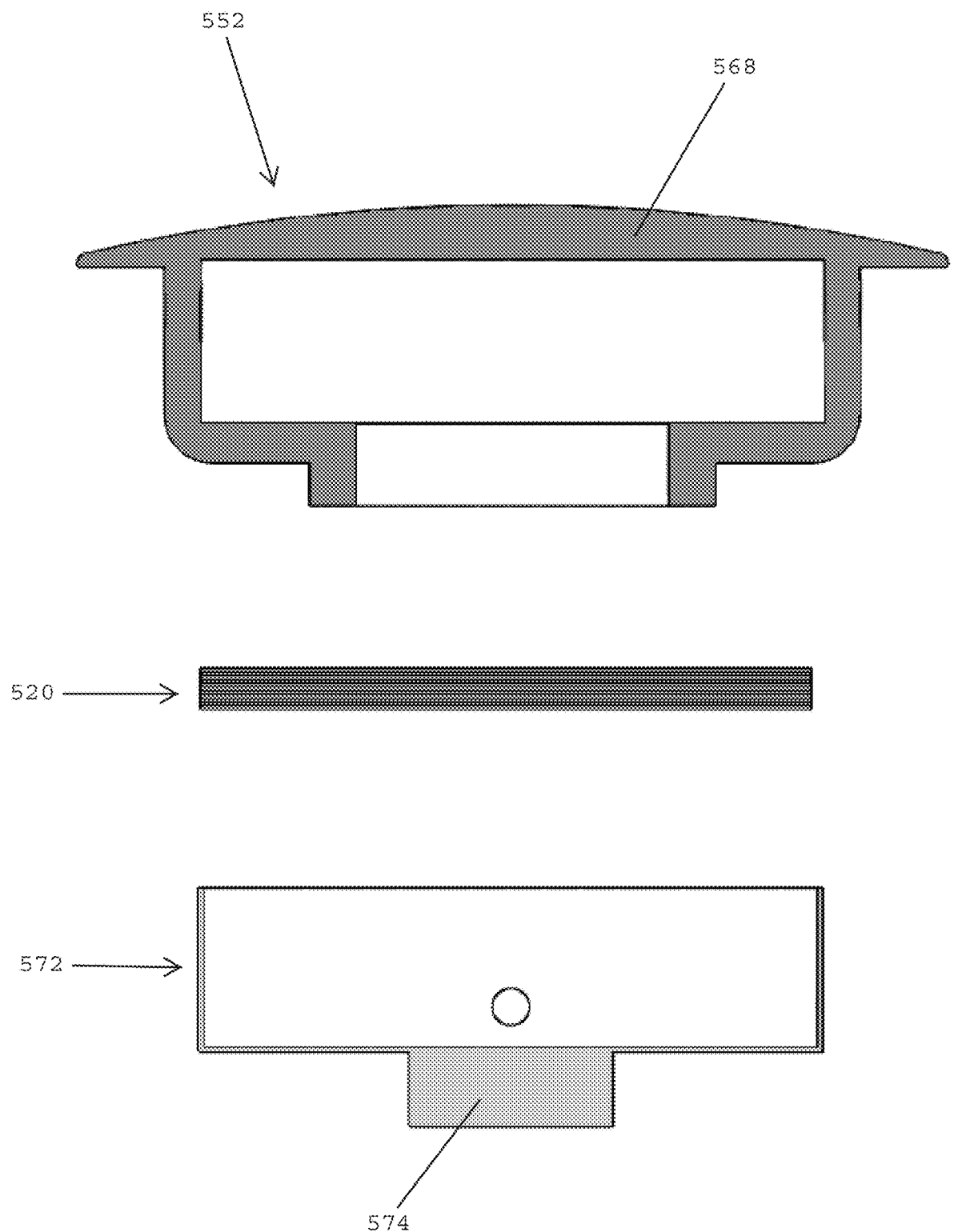
FIG. 15B is a cross-sectional view of the injection port assembly shown in FIG. 15A.

Referring to FIGS. 15A and 15B, in one embodiment, the self-sealing structure 520 shown and described above in FIGS. 14A and 14B may be incorporated into an injection port assembly 552 that includes an injection dome 568 and a needle guard 572 having a magnet 574.

Figure 16:
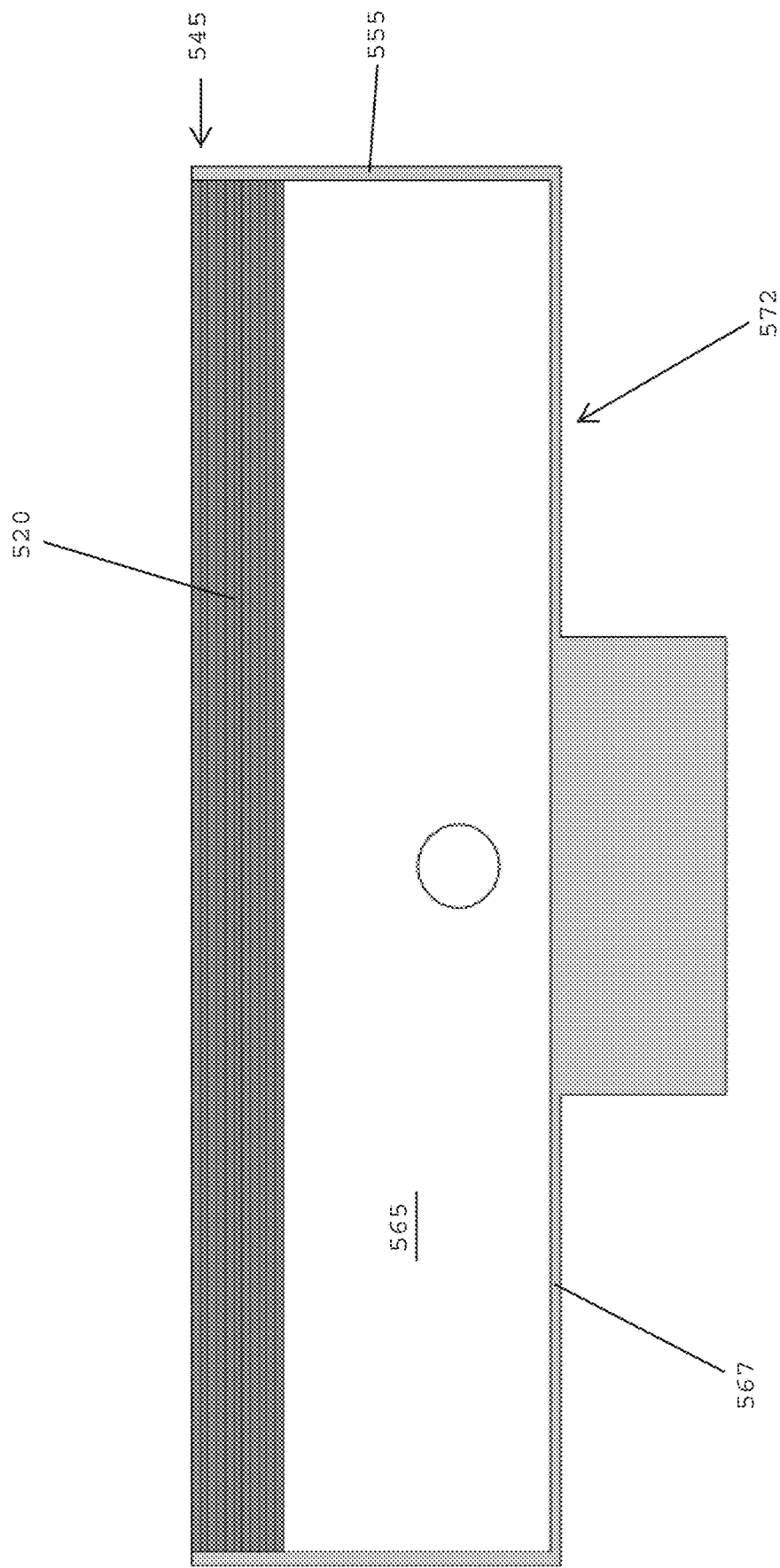
FIG. 16 is a cross-sectional view of the needle guard with magnet and the self-sealing sheet of FIGS. 15A and 15B after the needle guard with magnet and the self-sealing sheet have been assembled together, in accordance with one embodiment of the present patent application.

Referring to FIG. 16, in one embodiment, the self-sealing structure 520 is preferably secured to the upper end 545 of an outer wall 555 of the needle guard 572. The self-sealing structure 520 preferably completely covers the opening at the upper end 545 of the outer wall 555 to completely seal an enclosed chamber 565 disposed between a bottom surface of the implant shell sealing structures 520 and a bottom wall 567 of the needle guard 572.

Figure 17:
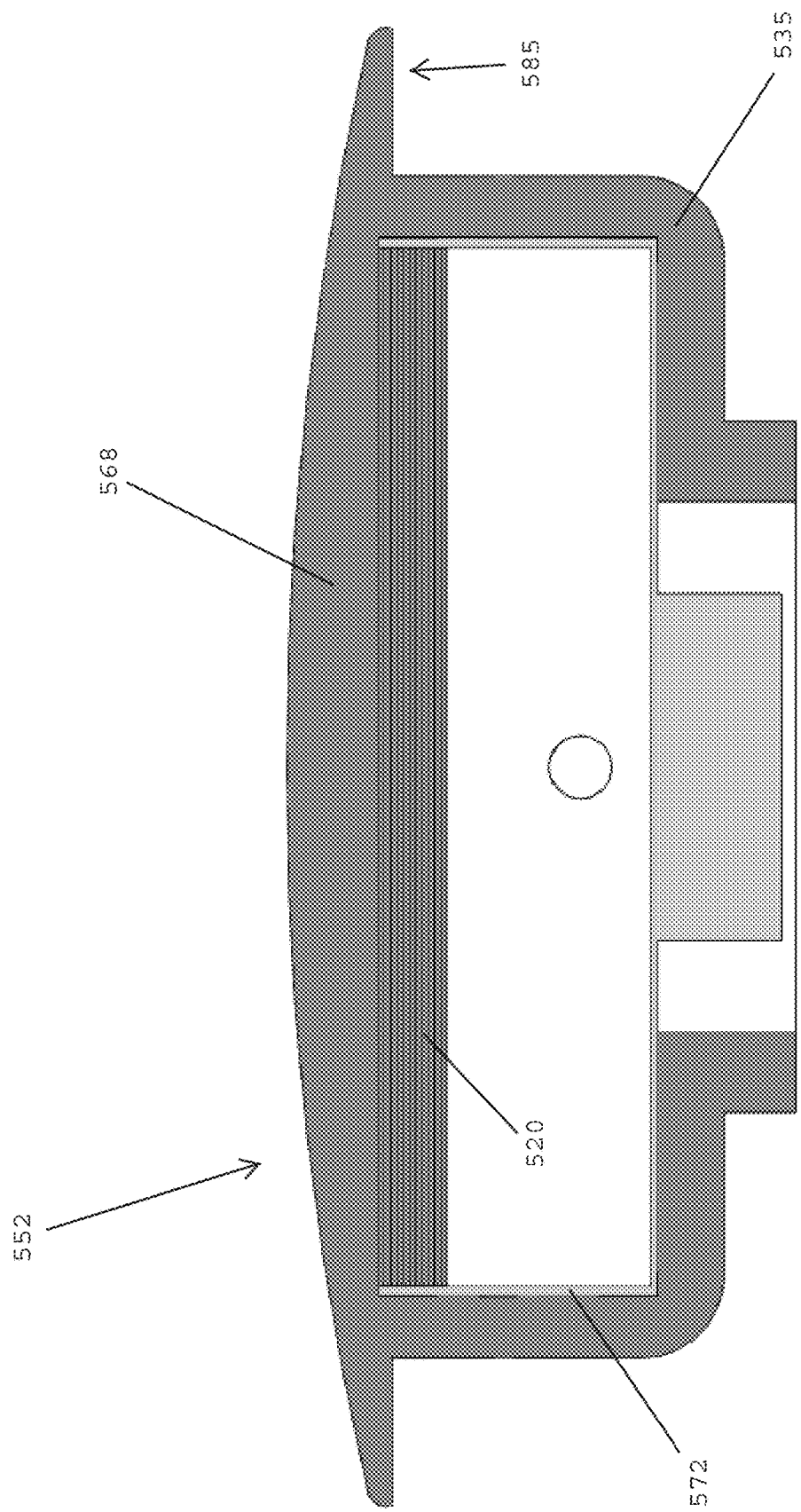
FIG. 17 is a cross-sectional view of an injection port assembly including an injection dome, a needle guard with magnet, and a self-sealing sheet, in accordance with one embodiment of the present patent application.

FIG. 17 shows an injection port assembly 552 including the self-sealing sheet 520 and the needle guard 572 of FIG. 16 assembled with the injection dome 568 shown in FIGS. 15A and 15B. The injection port assembly 552 may be inserted into an injection port opening of a shell of a breast tissue expander so that the sealing flange 585 of the injection dome 552 overlies the outer surface of the shell and the base 535 of the injection dome 568 passes through the injection port opening of the shell. In one embodiment, the base 535 of the injection dome 568 may also pass through the central opening of a self-sealing membrane as shown and described herein. In one embodiment, the anterior surface of the self-sealing structure 520 and the needle guard 572 of FIG. 16 may be attached directly to the inner surface of the shell without requiring an opening through the shell nor an opening through the self-sealing membrane.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A method of making a self-sealing membrane for a prosthetic device comprising:
    applying tension to a first layer of a cured elastomeric material to stretch said first layer;
    while said first layer remains stretched, applying a second layer of an uncured elastomeric material over a first major surface of said first layer and curing said second layer of said elastomeric material;
    after said second layer is cured, releasing the tension from said first layer, wherein said first layer returns to a non-stretched configuration for holding said second layer in contraction.

2. The method as claimed in claim 1, wherein said first layer comprises a shell for a prosthetic implant, and wherein the applying tension step comprises stretching said shell over a disk for exposing said first major surface.

3. The method as claimed in claim 1, wherein said disk has a flat major surface, and wherein stretching said shell over said disk conforms said first major surface of said shell to the shape of said flat major surface of said disk.

4. The method as claimed in claim 1, wherein said curing said second layer comprises applying heat to said second layer.

5. The method as claimed in claim 4, further comprising compressing said second layer into said first major surface of said first layer.

6. The method as claimed in claim 5, wherein the compressing step occurs during the applying heat step.

7. The method as claimed in claim 5, wherein the compressing step occurs before the applying heat step.

8. The method as claimed in claim 1, further comprising:
    while said first layer remains stretched, applying a third layer of an uncured elastomeric material over a second major surface of said first layer and curing said third layer of said elastomeric material;
    wherein after said second and third layers are cured and the tension is released from said first layer, said first layer returns to the non-stretched configuration for holding said second and third layers in contraction.

9. The method as claimed in claim 8, wherein said first layer comprises a silicone material, and wherein said second and third layers comprise a cured silicone elastomer.

10. The method as claimed in claim 1, wherein the applying tension step comprises using a fixture for stretching said first layer within a plane.

11. The method as claimed in claim 8, wherein said curing said second and third layers comprises applying heat to said second and third layers.

12. The method as claimed in claim 11, further comprising compressing said second and third layers into said respective first and second major surfaces of said first layer.

13. The method as claimed in claim 12, wherein the compressing step occurs during the applying heat step.

14. The method as claimed in claim 12, wherein the compressing step occurs before the applying heat step.

15. A self-sealing membrane for a prosthetic implant, said self-sealing membrane having a three-layer construction comprising:
    a middle layer of an elastomeric material having first and second major surfaces;
    a first outer layer of an elastomeric material overlying the first major surface of said middle layer;
    a second outer layer of an elastomeric material overlying the second major surface of said middle layer, wherein the middle layer is stretched prior to forming the three-layer construction such that the three-layer construction is movable from a stretched configuration to a non-stretched configuration, wherein, in said non-stretched configuration, said middle layer of said elastomeric material holds said first and second outer layers of said elastomeric material in contraction.

16. The self-sealing membrane as claimed in claim 15, wherein said self-sealing membrane is secured to an inner surface of a silicone shell of a prosthetic implant, and wherein said self-sealing membrane extends around an outer perimeter of an injection port of said prosthetic implant.

17. The self-sealing membrane as claimed in claim 15, wherein said self-sealing membrane is secured to a posterior region of a silicone shell of a prosthetic implant.

18. The self-sealing membrane as claimed in claim 17, wherein said self-sealing membrane defines a self-sealing base that covers a surface of said silicone shell at the posterior region of said silicone shell.

19. The self-sealing membrane as claimed in claim 15, wherein said self-sealing membrane is disposed within an injection port of a prosthetic implant.

20. The self-sealing membrane as claimed in claim 19, wherein said injection port includes a needle guard, and wherein self-sealing membrane covers an upper end of said needle guard.

21. A self-sealing sheet comprising two or more of said self-sealing membranes having the three-layer construction as claimed in claim 15, wherein major surfaces of adjacent ones of said self-sealing membranes having the three-layer construction are laminated together.

22. The self-sealing membrane as claimed in claim 21, wherein said self-sealing sheet is disposed within an injection port of a prosthetic implant.

23. The self-sealing membrane as claimed in claim 22, wherein said injection port of said prosthetic device includes a needle guard, and wherein self-sealing membrane covers an upper end of said needle guard.

24. The self-sealing sheet as claimed in claim 21, further comprising:
- a first self-sealing membrane having the three-layer construction;
- a second self-sealing membrane having the three-layer construction being laminated to an exposed major surface of said first self-sealing membrane;
- a third self-sealing membrane having the three-layer construction being laminated to an exposed major surface of said second self-sealing membrane.

* * * * *